(12) United States Patent
Saldivar

(10) Patent No.: US 7,807,106 B2
(45) Date of Patent: Oct. 5, 2010

(54) APPARATUS AND METHOD TO MEASURE PLATELET CONTRACTILITY

(76) Inventor: Enrique Saldivar, 305-B. Whispering Willow Dr., Santee, CA (US) 92071

( * ) Notice: Subject to any disclaimer, the term of this patent is extended or adjusted under 35 U.S.C. 154(b) by 481 days.

(21) Appl. No.: 11/975,893

(22) Filed: Oct. 22, 2007

(65) Prior Publication Data

US 2008/0286823 A1    Nov. 20, 2008

(51) Int. Cl.
*G01N 33/00* (2006.01)
(52) U.S. Cl. .......................................... 422/73
(58) Field of Classification Search ........................ None
See application file for complete search history.

(56) References Cited

U.S. PATENT DOCUMENTS

| 4,986,964 | A | * | 1/1991 | Carr et al. ...................... 422/73 |
| 5,293,772 | A | * | 3/1994 | Carr, Jr. ...................... 73/64.41 |
| 6,573,104 | B2 | * | 6/2003 | Carr et al. ...................... 436/69 |

* cited by examiner

*Primary Examiner*—Jon P Weber
*Assistant Examiner*—Satyendra K Singh
(74) *Attorney, Agent, or Firm*—Fuess & Davidenas

(57) ABSTRACT

An apparatus and method for measuring blood platelet contractility, hereinafter called a "retractometer" is disclosed. Also disclosed is a system apparatus and method for automatically measuring platelet contractility in a plurality of samples, having an array of retractometer units and an electronic solenoid valve controller to fully automate screening in clinical and research situations and save costs in labor.

4 Claims, 17 Drawing Sheets

APPARATUS AND METHOD TO MEASURE PLATELET CONTRACTILITY

This application claims the benefit of priority under 35 U.S.C. §121 of application Ser. No. 10/632,532, filed Aug. 1, 2003, which is incorporated by reference herein. This work was supported by National Institute of Health Grant No. R29-HL57430-01.

BACKGROUND OF THE INVENTION

1. Field of the Invention

The present invention generally concerns blood clotting components and mechanisms.

The present invention particularly concerns new devices and methods for studying clotting mechanisms and factors. More specifically, an apparatus and method for measuring and monitoring health and activity of platelets and other clotting factors are described. Most specifically, a clot retractometer and its method of use are provided to measure clot contractility forces as a means to provide a single point "funnel detection" procedure useful in aiding physiological and clinical research and patient diagnosis and monitoring of many diseases, as well as screening populations.

2. Description of Related Art

Introduction

Everyone has seen a clot form as a result of injury to tissue, such as, for example, a scrape, puncture or a bleeding nose. However, the formation of a clot is a complex, cascading process that is still not completely elucidated, either physiologically or clinically. The clotting phenomenon, or lack thereof, is manifest in numerous clinical conditions, and is relevant to their prognosis.

In response to soft tissue injury, the haemostatic mechanism is activated to stop bleeding and restore vascular integrity. Blood protein and cellular interactions lead to the formation of a platelet plug and ultimately generation of clot comprising platelets and protein fibers. These reactions have to occur rapidly because the amount of blood lost is dependent on the time required to arrest the bleeding. Although rapid stoppage of blood loss is critical in some cases, inappropriate induction of clotting can have devastating effects such as decreased blood flow to the organs and resultant ischemic damage, such as heart attacks and stroke if the clot is not solubilised. To counterbalance these potentially severe consequences the haemostatic system is uses certain clotting inhibitors, and clot-dissolving enzymes.

Following vascular damage, the exposure of flowing platelets to the subendothelial lining allows the establishment of adhesive interactions with the immobilized surfaces. Platelets then become activated due to contact with thrombogenic substrates and stimulation by locally released or generated agonists. Subsequent platelet deposition relies on the binding of plasma-soluble adhesive molecules, and on the externalization of adhesive molecules from the platelets' granular reservoirs, this process conditions the newly recruited monolayer of platelets to become the reactive surface for continuing platelet accrual.

Immediately after platelet arrest, the clotting process begins by the participation of platelet released substances and fluid phase coagulation factors. Initiation of the coagulation cascade results in the conversion of prothrombin to thrombin (a serine protease). Thrombin cleaves two pairs of peptides (fibrinopeptides A and B) from the aminoterminal ends of the Aα and Bβ chains of the fibrinogen molecule. Cleavage of fibrinopeptide-A is sufficient to initiate clot assembly (4). The monomer units formed initiate a self-assembly process of forming protofibrils. Weak lateral interactions between protofibers increase as the protofibers lengthen, resulting in their alignment and coalescence, to ultimately yield fibers. This process leads to the formation of a network composed of fibrin polymers and spaces filled with fluid. Once the fibrin network is formed, the platelets begin to contract, resulting in a pull on the strands of the fibrin network. Platelet contraction requires active restructuring of the platelet cytoskeleton.

Dynamic rearrangements in the cytoskeleton are crucial during platelet activation in both, initial platelet adhesion to surfaces (see FIG. 1) and platelet to platelet cohesion. Actin polymerization in non-stimulated platelets is limited by monomer-sequestering proteins such as thymosin β4, profilin and barbed end-capping proteins such as gelsolin (5-7). Under these conditions, around 2,000 actin filaments are distributed in the cytoskeleton and in the membrane skeleton right under the inner surface of the plasma membrane (8). After the stimulation by strong agonists, there is a rapid increase in actin polymerization, with reorganization of the two actin networks, resulting in a change of shape with formation of filopodia and lamellipodia at the cell periphery. This is followed by redistribution of actin and other cytoskeletal and signaling proteins form the membrane skeleton to the cytoskeleton (9; 10). Platelet spreading is associated with the appearance of actin stress fibers and focal-adhesion-like structures that contain clusters of integrins and vinculin (11). Small GTPases of the Rho family—such as cdc42Hs, Rac, and Rho—have been implicated in the formation of filopodia, lamellipodia and focal adhesion plaques in many cell types (12), and the same may occur in platelets.

Under normal conditions, the coagulation system remains in a fine balance. Pathologic alterations of the system may induce a risk of hemorrhage or increase the potential for thrombosis. An example of the former would be the bleeding disorder of hemophilia, which results from a low activity of Factor VIII, a blood clotting protein. An example of the latter would be recurrent venous thrombosis in individuals who have decreased levels of the coagulation inhibitor antithrombin III. Patients with decreased ability to remove clots, decreased fibrinolytic potential, are also at risk for thrombosis To counterbalance the abovementioned mechanisms that precipitate platelet activation, platelets are downregulated by the anti-thrombotic potential of normal endothelial cells, in vivo, and by substances produced by the activated platelets. The majority of pathways that result in inhibition of platelet aggregation and procoagulant activities act by increasing the internal level of cyclic AMP, which activates the cyclic AMP-dependent protein-kinase. This leads to serine-threonine phosphorylation of an array of substrates.

Experimentally, the result of the platelet contraction and the tension applied on the fibrin network strands is observed in vitro as clot retraction. Macroscopically, clot retraction is seen as a dramatic reduction in clot volume in a process that expels the fluid trapped inside the clot. Although the physiological role of clot retraction is not completely understood, it is assumed that it helps in approximating the edges of a tissue defect and in concentrating the clot in the area of injury (4). One issue that it is clear in clot retraction is that in order for this process to occur normally all haemostatic mechanisms must act in synchrony. The two primary requirements for proper clot retraction to occur are the formation of an appropriate fibrin network and healthy platelets, capable of contracting and anchoring the fibrin network. The structure and formation of the fibrin network are sensitive to pH, ionic strength, calcium concentration, plasma proteins, platelet release products, leukocyte materials, etc. (4).

Examples of pathological conditions that affect the structure of the fibrin network are diabetes mellitus and multiple myeloma (4; 13). Healthy platelets need to express the integrin $\alpha_{IIb}\beta_3$ on their surface to properly anchor the fibrin strands and they need to be metabolically fit for the task. Examples of pathological conditions that affect platelet metabolism are diabetes mellitus and uremia (14). Also, the age of platelets affects their performance, this aspect is particularly important for transfusion purposes.

The wide spectrum of processes involved in clot retraction, including biochemical, biorheological and biomechanical mechanisms, in conjunction with fine controlling and orchestration mechanisms, makes clot retraction a very desirable focus point that represents the well-being of all the steps required for this event to take place. This approach of "funnel detection" yields excellent means for population screening and individual patient monitoring for clinical progress.

Current State-of-the-Art

In clinical practice, the measurement of platelet viability has been used mainly to set standards for appropriate storage and handling of platelet concentrates. These techniques include estimation of the life-span after storage with radiolabeling, measuring the reduction of bleeding time, and semi-quantitative estimation of platelets to form aggregates in vitro with the use of platelet aggregometers. These techniques, however, are not routinely used to evaluate platelet performance. A more practical estimation of the capacity of platelets to function normally appears to be retention of shape, ATP content and function in the osmotic reversal reaction (15).

Methods Currently Used to Evaluate Clot Retraction

A common method utilized to evaluate clot retraction is quantitation of the fluid volume expelled by the clot during retraction, and estimation of the volume of the residual clot (16). This is a qualitative essay that does not provide information about the force generated during clot retraction.

Another known method involves the formation of cylinders or strips of clots, which are then immobilized on one end and anchored to a force transducer (17) on the other. This technique requires mechanical manipulation of the sample and bathing of the clots in a foreign substance that may alter the natural process of clot retraction.

Yet another technique utilizes a rheometer to measure the normal force development during clotting and retraction (18). An important limitation of this technique is the high cost of the equipment.

A method described by Carr in U.S. Pat. Nos. 4,986,964; 5,293,772 and 5,205,159 directly measures the force developed by platelets during clot retraction. Carr's apparatus consists of a cup in which the fluid sample (before clotting) is placed. The opening of the cup is covered by an upper plate, which is coupled to a steel arm attached to a force transducer. As the clot retracts, the force generated is transmitted to the force transducer, where it is measured (1; 4; 13; 14). Although this is a very reliable method, the cost per measurement is high, because this method allows only the measurement of one sample at a time. Also, this equipment has the added complication of the high precision required for its alignment and setup.

Therefore, it would be advantageous to have a low-cost, reliable method for the quantitation and monitoring of the force developed during clot retraction. This would provide a simple way to assess several variables of clinical relevance that converge into one single measurable variable, i.e. using the abovementioned funnel detection philosophy. Moreover, what is needed is an easy-to-use and economical device to accurately measure the force developed during clot retraction. This device should be self-contained in order to minimize exposure to biohazardous materials. Such a device would have a broad spectrum of clinical applications, including, for example, patient evaluation and population screening for pathological conditions.

SUMMARY OF THE INVENTION

The primary object of this invention is to provide a novel platelet retractometer that will measure the force developed by platelets during blood clot retraction.

Another object in accordance with the present invention is a device that can automatically measure the force developed by platelets during clot retraction, is easy and inexpensive to operate, and provides no exposure of the operator to biohazardous materials.

A further, most preferred object is to provide a method for measuring the force developed by platelets during clot retraction, as well as its clinical applications, in both research and patient monitoring. The clinical applications comprise all conditions in which platelet viability and platelet metabolism are impaired, including, but not limited to, diabetes mellitus, chemotherapy, and monitoring of platelet aging for blood transfusion. In experimental applications, the device will increase the scope of study in platelet biology by bringing a user-friendly ready-to-use method useful to dissect the mechanisms involved in platelet contraction in both, physiological and pathological conditions.

In accordance with these objects, this invention contemplates an apparatus for measuring blood platelet contractility, hereinafter called a "retractometer." The retractometer has a spherical rigid chamber with an opening in its dorsal aspect. Found inside this chamber is a smaller, spherical, flexible membrane chamber concentrically aligned and isolated from the larger rigid chamber, creating a void space between the walls of the rigid and flexible chambers. The flexible membrane chamber also has an opening in its upper aspect, smaller than and coaxial to the opening in the rigid chamber. There is a tube attached at the opening, leading out of the flexible chamber concentrically and in perpendicular axis through the opening in the rigid chamber. This concentric alignment of chambers creates a void space that is isolated from the void space of the flexible inner chamber. A second tubular passage is connected to the valve at one end and in perpendicular alignment to the first passage. A pressure transducer is connected to the distal end of this second tube. Thus, any force exerted on the flexible chamber to alter its diameter would be measured by the pressure transducer. The membrane chamber can be manufactured from latex by dipping a mold and withdrawing a thin spherical bag with an opening created by a shaft attached to a spherical mold. The flexible membrane can be latex or any other suitable material.

In further accordance with these objects, this invention contemplates an alternative retractometer having similar spherical rigid and flexible chambers, and openings in their upper aspect isolating the two chambers from each other and creating a void space between their walls. The variation from the abovedescribed setup is that the tubular chamber leading out of the flexible chamber concentrically and in perpendicular axis through the opening in the rigid chamber, has both ends sealed. This creates a void space that is isolated from the void space of the flexible inner chamber. Through this tubular chamber, runs a glass capillary tubing, coaxial to and longer than the tubular chamber, passing through both ends of the sealed tubular chamber. This creates a continuous passage from outside of the apparatus to the void space of the inner flexible chamber. The distal opening of the capillary tubing is plugged before directly reading the force applied by the retracting clot as the height of the fluid column inside the capillary. This plug can either be a removable type, like a cap or stopper, or a sealed type that is opened by breaking the capillary at an etched or scored point above the sealed tube.

The advantage of this embodiment is that direct readings can be taken, with no need for electronic measuring equipment. The disadvantage is that it does not readily lend itself to automation except by optical readings.

A more specific and preferred embodiment of this invention is an automated system for measuring blood platelet contractility of a plurality of samples having an array of retractometer units with valves as described hereinabove. Each unit retractometer is a separate apparatus for measuring blood platelet contractility of a single sample. As described above, it comprises a spherical rigid chamber having an opening in its upper aspect, a smaller, spherical, flexible membrane chamber placed concentrically within the rigid chamber, creating a void space between the walls of the rigid and flexible chambers, and having an opening in its upper aspect that is smaller than and coaxial to the opening in the rigid chamber. A first, attached contiguous tubular passage leads out of the flexible chamber concentrically and in perpendicular axis through the opening in the rigid chamber, creating a void space that is isolated from the void space of the flexible inner chamber. A two-way valve is attached to the distal end of the tubular passage, which in turn, is connected to a second tubular passage. The end distal to the valve is connected to a common pressure transducer. The valves are operated automatically by solenoids, energized and regulated by an electronic circuit. This circuitry is programmed to choose and operate the solenoid valves in a predetermined order written in software by the inventors.

An equally preferred embodiment in accordance with this invention is an electronic solenoid valve controller to fully automate a system comprising a number of retractometers and save costs in labor. This embodiment is a system apparatus for automatically measuring platelet contractility in a plurality of samples. The system has a pump mechanically connected to a pump motor, which in turn is electronically connected to a microprocessor having a plurality of pins. One pin is used to turn the pump motor on; a second pin to move fluid in the pump in one direction; a third pin to move fluid in the pump in an opposite direction; and at least one of the remainder of the pins to activate each of an array of solenoid valves. The system also has a voltage divider used to establish the position of the fluid in the pump. There is a fluid conduit connecting the pump to a hydraulic system having a manifold that connects the pump to each of a plurality of retractometers controlled by solenoid valves. Each retractometer communicates with one of the solenoid valves. A pressure transducer reads each pressure and sends the reading to an analog to digital (A/D) converter connected electronically to the transducer, the pump motor, the microprocessor, and a computer.

Basically, sequence of events is as follows. A readout position voltage from the voltage divider is entered through the (A/D) converter to the microprocessor, which determines the direction of flow in the pump and activates the pump to adjust the fluid pressure within the system. The pressure is then measured by the pressure transducer connected electronically to the A/D converter, and a target pressure is registered in the microprocessor memory, which is subsequently recorded and displayed by the computer.

This apparatus embodiment may have a pump that moves fluid with a sliding piston. Preferably, the pump is a syringe controlled by a step motor with very fine gradations. Preferably, the apparatus has an array of eight solenoid valves, each valve, communicating with one of eight retractometers. More preferably, the system apparatus is expandable by addition of retractometers and valves. Most preferably, the retractometers are packaged in a cartridge, such that one cartridge is removed after sampling and replaced with another having additional samples, and so on.

The apparatus is protected by a protection valve located at the entrance to the pressure transducer to prevent damage to the system and a second protection valve to control access to a fluid reservoir. The subroutines in the analysis program are burnt into the microprocessor.

A most preferred embodiment in accordance with this invention is a method for measuring blood platelet contractility. The method comprises the steps of preparing a retractometer according to this invention by applying adhesive to the surface of the inner flexible membrane to avoid slippage of clots. The adhesive can be any suitable substance, for example, collagen Type I suspension. The coated flexible membrane is then pressure conditioned by mounting it on a rubber stopper pierced by a hypodermic type needle attached to a two-way valve. A syringe is attached to one opening of the valve and a second needle is attached to a second opening of the valve, making certain that the reach of the two needles is identical.

Next, the membrane chamber is slightly pressurized, the valve to the syringe is closed, communication is opened to ambient fluid. In this manner, the inner and ambient pressures are allowed to equilibrate by siphoning. The fluid level inside the capillary is adjusted to "zero pressure" level.

The second step involves loading of the sample into the void created between the two chambers, surrounding and in contact with the outside surface of the flexible membrane chamber. A small amount of oil is added over the sample to avoid drying out. The sample is then allowed, or induced, to clot and the force of the clot retraction is measured in a pressure transducer and recorded.

Also contemplated by this invention is a method for automatically measuring a number of samples in a number of retractometers to determine the strength of platelet contractility. A first step requires calibration of the apparatus above. This entails the microprocessor reading all initial pressures in all retractometers sequentially by opening each solenoid valve, opening the protection valve, measuring the voltage in the pressure transducer and storing the measured value in the temporary memory of the microprocessor. This process is repeated until all the initial pressure values are registered as target values for each of the retractometers. The second step adjusts the value of the hydraulics by opening the protection valve only and activating the pump until the target value is reached. The sample is then loaded into the retractometers, and clot formation is induced. The third step requires opening of the sample valve, measuring the pressure, and closing the sample valve, in that sequence. The measured values are then sent to a text file in a computer, and the new measured value for each retractometer becomes the next target value. This third step is repeated until all samples are measured. The entire process of measuring the clotted samples takes less than one minute.

The methods described here are useful in determining platelet activity. The ability to determine platelet activity, and contractile strength, is more specifically useful in determining viability of stored blood products. Determining forces of contractility is particularly useful in diagnosis or prognosis of various diseases in patients. Because each of the components associated with clotting is the result of a myriad of intermediate steps, clot retraction is an excellent candidate for "funnel detection" where with one simple measurement it is possible to unmask a vast array of pathological stages. Funnel detection methods are particularly important in population screening studies.

Still further embodiments and advantages of the invention will become apparent to those skilled in the art upon reading the entire disclosure contained herein.

It is stressed that the figures above represent only certain fully tested working examples and do not limit the invention to these precise illustrations.

DESCRIPTION OF THE PREFERRED EMBODIMENTS

Introduction

After in vitro clot formation, the fibrin meshwork entraps virtually all the serum and the cellular components of blood. Within minutes to hours, the platelets in the clot contract, expelling a very large fraction of the serum. This process is known as clot retraction. Although the physiological relevance of clot retraction is still not fully understood, the fact that platelets are needed for this process to take place is well documented (1). There is strong experimental evidence that suggests the participation of an actinomyosin contractile mechanism as well as the involvement of the platelet $\alpha_{IIb}\beta_3$ in the process (2;3).

The present invention is based on the rationale that the development of a reliable method for the study of clot retraction will bring not only a useful tool to elucidate the mechanisms involved in the physiological mechanisms but also an important tool for the monitoring of the overall well-being of the platelets in a blood sample. This invention will potentially yield an important diagnostic tool for the monitoring and detection of pathological states, as well as an easy-to-use tool for the monitoring of platelet viability for transfusion purposes.

MATERIALS AND METHODS

In order to develop the instant invention, certain relevant parameters had to be elucidated. In the examples hereinbelow, are described determinations of platelet activation under certain conditions, as well as manipulations of clot geometry.

EXAMPLE 1

Perfusion Studies
Methods

Blood obtained from healthy volunteers was mixed with D-phenyl alanyl-L-prolyl-L-arginine chloromethyl ketone dihydrochloride (PPACK, 93:M) to prevent clotting. The platelet count was adjusted to 10,000/µl to reduce the number of events on the surface and facilitate image analysis. Perfusion experiments were conducted in a parallel plate flow chamber at 37° C. (3) using type I collagen fibrils as reactive substrate onto glass coverslips. The interaction of flowing platelets with the surface was evaluated in real time by reflection interference contrast microscopy (RICM) using a Zeiss Axiovert 135M microscope. In this technique, interference colors indicate the distance between two surfaces, such as cellular membranes and a substrate coated on glass. On a gray scale, zero-order black indicates a separation of 4-12 nm, and white a distance>20-30 nm (15; 19). Experiments were recorded on S-VHS videotape at the rate of 30 frames per second and analyzed off-line with Metamorph (Universal Imaging) software.

Results

Platelet Interaction with Surface Immobilized Collagen Type I.

Figure 1:
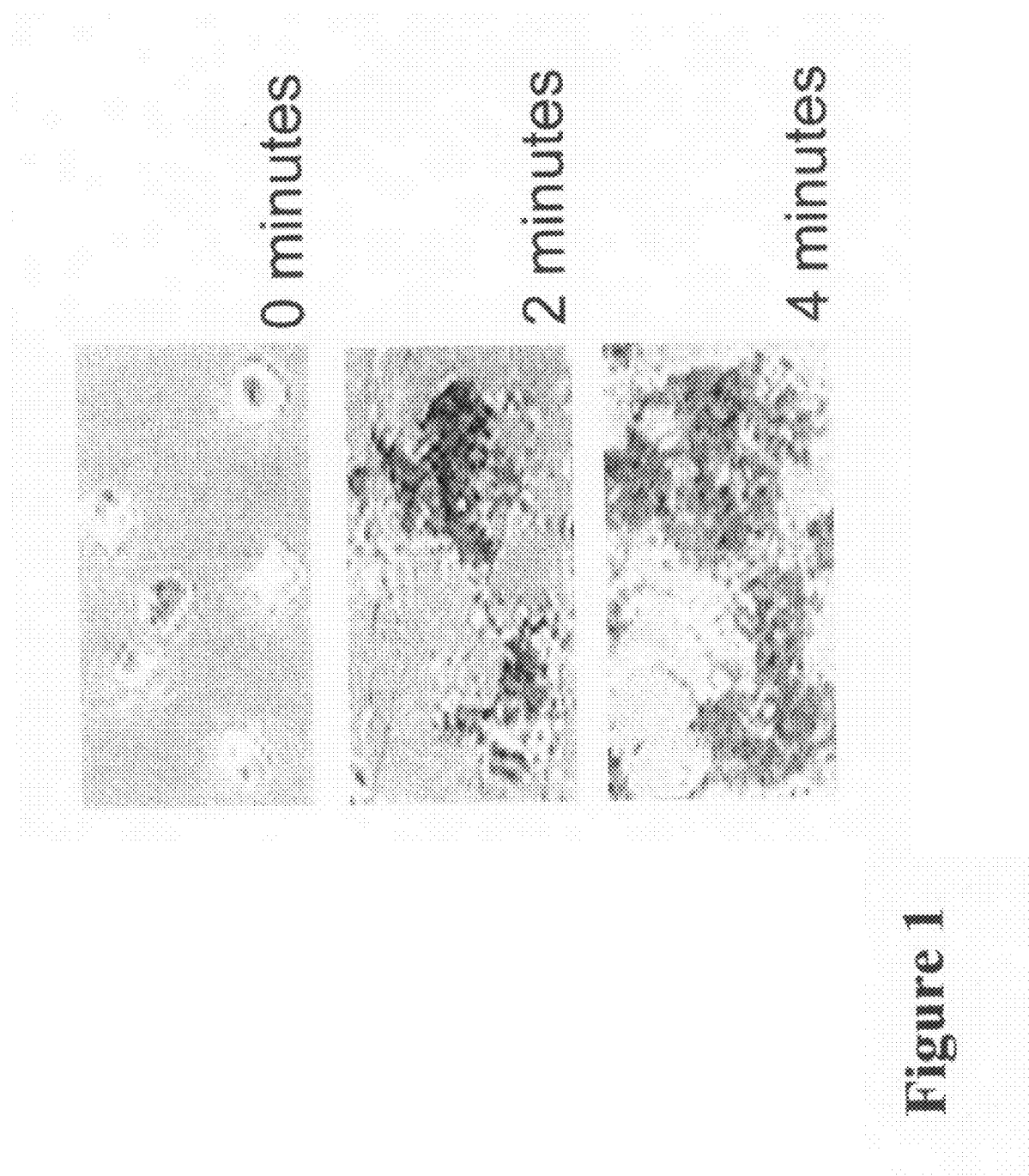
FIG. 1 shows Platelet interaction with surface immobilized collagen type I. RICM images show platelets in a flow field. On a gray scale, black indicates a distance from the surface of 4-12 nm; white of >20-30 nm. The time after initiation of the experiment is shown at the right side of each panel. For this experiment the platelet count was reduced to 10,000 platelets per μl.

The top panel in FIG. 1 (0 minutes) shows the native spheroidal shape of the platelets, before activation. A few seconds after the initial platelet adhesion occurs, the first signs of activation are seen as dramatic shape changes and subsequent adhesion of the platelet membrane to the reactive surface. The other panels (2 and 4 minutes) show the activation and spreading that two single platelets undergo. Of notice is the large area that a single platelet can cover. This experiment shows the large amount of "membrane reservoir" contained by the relatively small platelets. After activation, the platelets initiate contraction, resulting in their deformation and clot formation. This phenomenon is not observed in the photographs shown here because the platelets are attached to a non-deformable surface (glass); however, the platelets increase the tension on their membrane due to the abovementioned cytoskeleton rearrangement.

EXAMPLE 2

In order to demonstrate some of the technical capabilities currently being developed in the Inventors' laboratory, a summary of the development of a technique to create an upscale replica of an actual thrombus is presented below. The geometrical data of the thrombus are obtained with confocal microscopy while the blood is continuously flowing as previously reported (20). This technique was developed to study the flow field around a thrombus in an upscale chamber. By matching the Reynolds number, it is possible to determine the flow path in the microscopic realm, based on the similarity principle.

Figure 2:
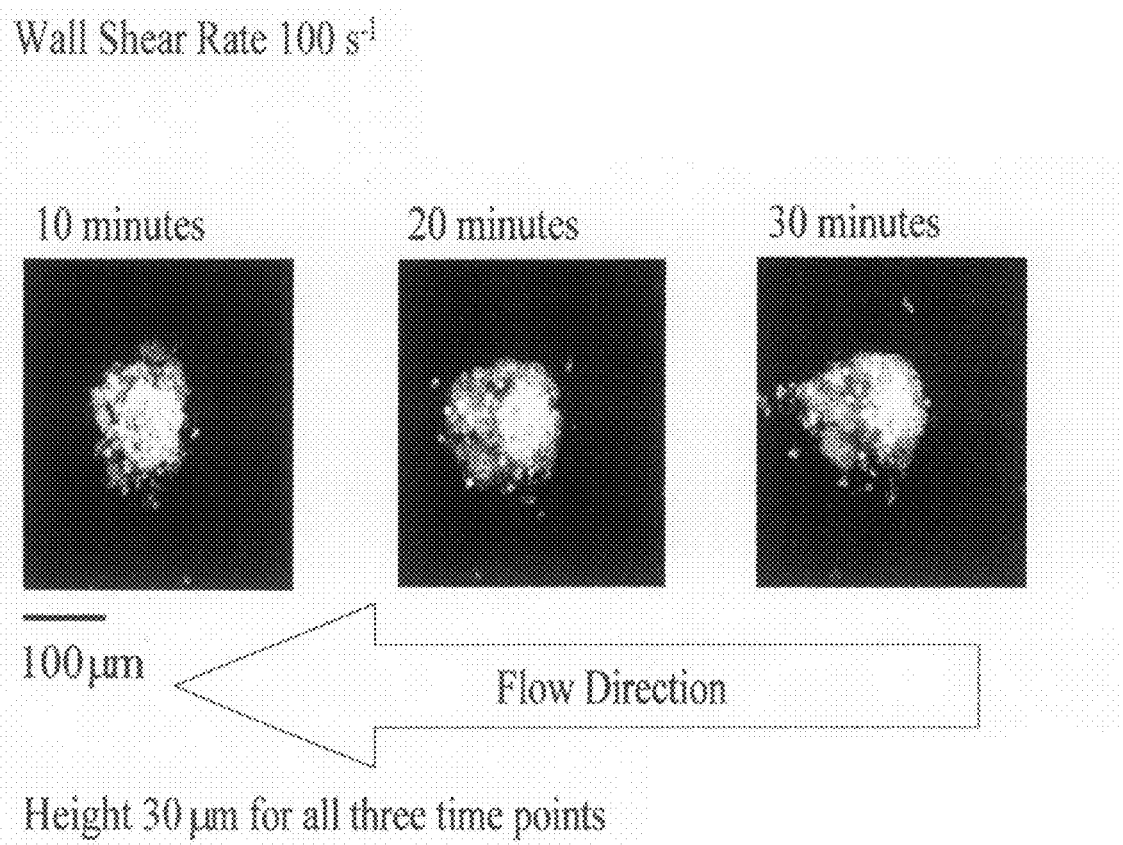
FIG. 2 shows the evolution of an isolated thrombus at 100 $s^{-1}$. For the experiment shown here, development of a single thrombus was recorded. This image shows the thrombus once it is developed (>10 minutes) to observe the grow changes. Each image corresponds to the summation of a series of confocal images. Of notice is the peculiar growth pattern of the thrombus. Platelet deposition appears to occur in the downstream areas.

The evolution of an isolated thrombus at 100 s$^{-1}$ is depicted in FIG. 2. For the experiment shown here, a single thrombus was recorded from initiation of the flow. This image shows the growth changes in the thrombus once it is developed (>10 minutes) to 30 minutes. Each image is derived from the summation of a series of confocal image slices. Of note is the peculiar growth pattern of the thrombus. Platelet deposition appears to occur in the downstream areas.

EXAMPLE 3

Below, Inventors describe their technical solution to create an upscale three-dimensional (3-D) model of a thrombus based on the information obtained with confocal microscopy.

As a first step, Inventors decided to investigate the already available techniques for 3-D rapid prototyping. A commonly used technique is stereolithography, which uses step-wise planar buildup of the object, based on the solidification of a photoresin by a laser beam. After each layer is cured, the object is lowered into a fluid resin pool by a distance equal to the vertical resolution of the system. This technique appears to be adequate in view of the complex geometries that it can handle.

The main practical difficulty in merging confocal microscopy and stereolithography is the lack of compatibility of the data. Confocal microscopy renders the data in a series of images (TIFF files in our system). These images are represented by a series of pixels with a given grayscale value, and the images are separated by the distance of the confocal sections (1 µm in this case). Stereolithography, on the other hand, uses ASCII files that contain coordinates of the surfaces surrounding the object. This format has the practical advantage of possessing the capability to rotate objects to an orientation that facilitates the manufacturing process. Inventors developed the series of steps that successfully led to the generation of a Stereolithography file from the original images of the experimental data.

EXAMPLE 4

Generation of Stereolithography Files from Confocal Data

The confocal microscopy images obtained were preprocessed with a 3×3 median filter, in order to minimize noise originated by the flow. The images were then translated into a voxel space with a software package written by Inventors specifically for this purpose. This package maintains the relative positions of the measured objects in a Cartesian three-dimensional space. The voxel representation of the microscopic field was then used with AVS release 5.3 (Application Visual Systems, Inc., Waltham, Mass.) to render the three-dimensional field. This software package allows the operator to interpolate a surface (isosurface) between contiguous voxels with an intensity above a preset threshold. This isosurface is comprised of a series of triangles, each triangle being a "surface unit." The coordinates of these surface units were then stored in a geometry information file. The geometry file was then translated into an "STL" file (standard input format for stereolithography) with a software package written by Inventors specifically for this purpose. The STL file contains the coordinates of the vortices of the surface units and a normal vector pointing outside of the body of the object to be materialized. During the fabrication process, a scale factor was included to yield the desired dimensions. A graphic representation of the file generation is shown in FIG. 3.

Graphic Representation of the STL File Generation.

Figure 3:
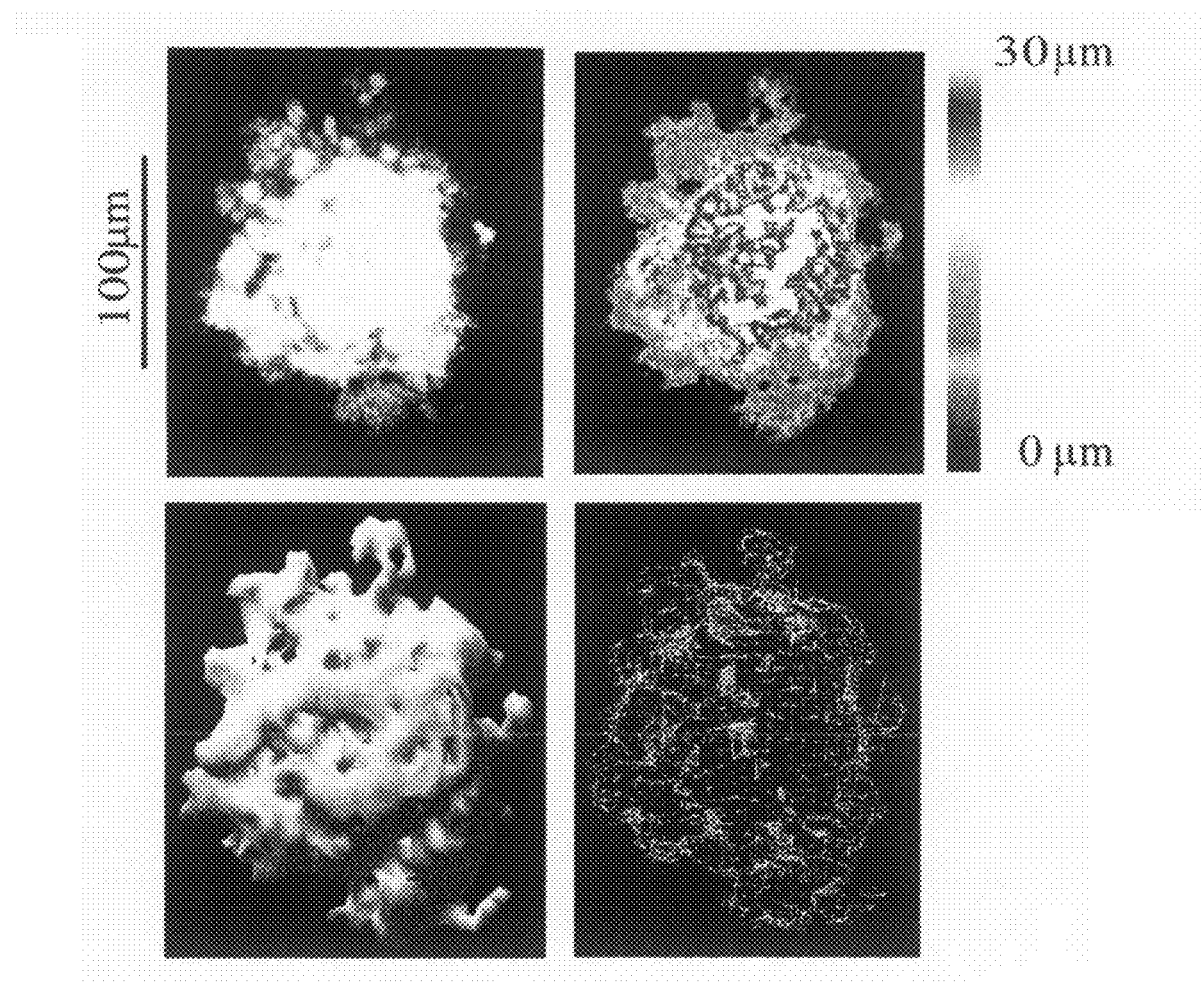
FIG. 3 is a graphic representation of the STL file generation. For the experiment shown in this figure, an isolated thrombus obtained with collagen spray was used. The wall shear rate was $100^{s-1}$ and the data presented correspond to images taken after 10 minutes of flow. The geometry reconstructed here corresponds to the thrombus shown in the early time of FIG. 2

For the experiment shown in this FIG. 3, an isolated thrombus obtained with collagen spray was used. The wall shear rate was 100$^{s-1}$ and the data presented correspond to images taken after 10 minutes of flow. The geometry reconstructed here corresponds to the thrombus shown in the early time of FIG. 2. The upper left panel shows a summation of all the confocal images obtained from a real thrombus. The upper right panel shows the topographical representation of the thrombus in pseudocolor. The bar on the right shows the color code for the height in micrometers. The lower left panel shows the 3-D representation rendered with AVS, as described above. Although it is possible to orient the geometry to any position, a planar view was chosen for easier comparison of the 3-D representation with the original data.

The lower right panel shows a graphic representation of the STL file. The graph shows a wire model of the file, with the orientation identical to the previous panels. The "hedgehog" appearance is due to normal vectors pointing outside of the body, as described in the method. For clarity, the normal vectors are shown in blue, and the wire model in white. This type of graphic representation is not necessary for the actual fabrication process, but it is useful for error detection in the creation of the files and overall quality evaluation of the process. In the graph, the complexity of the surface and the large number of triangles necessary to reconstruct such a complex geometry can be appreciated.

Figure 4:
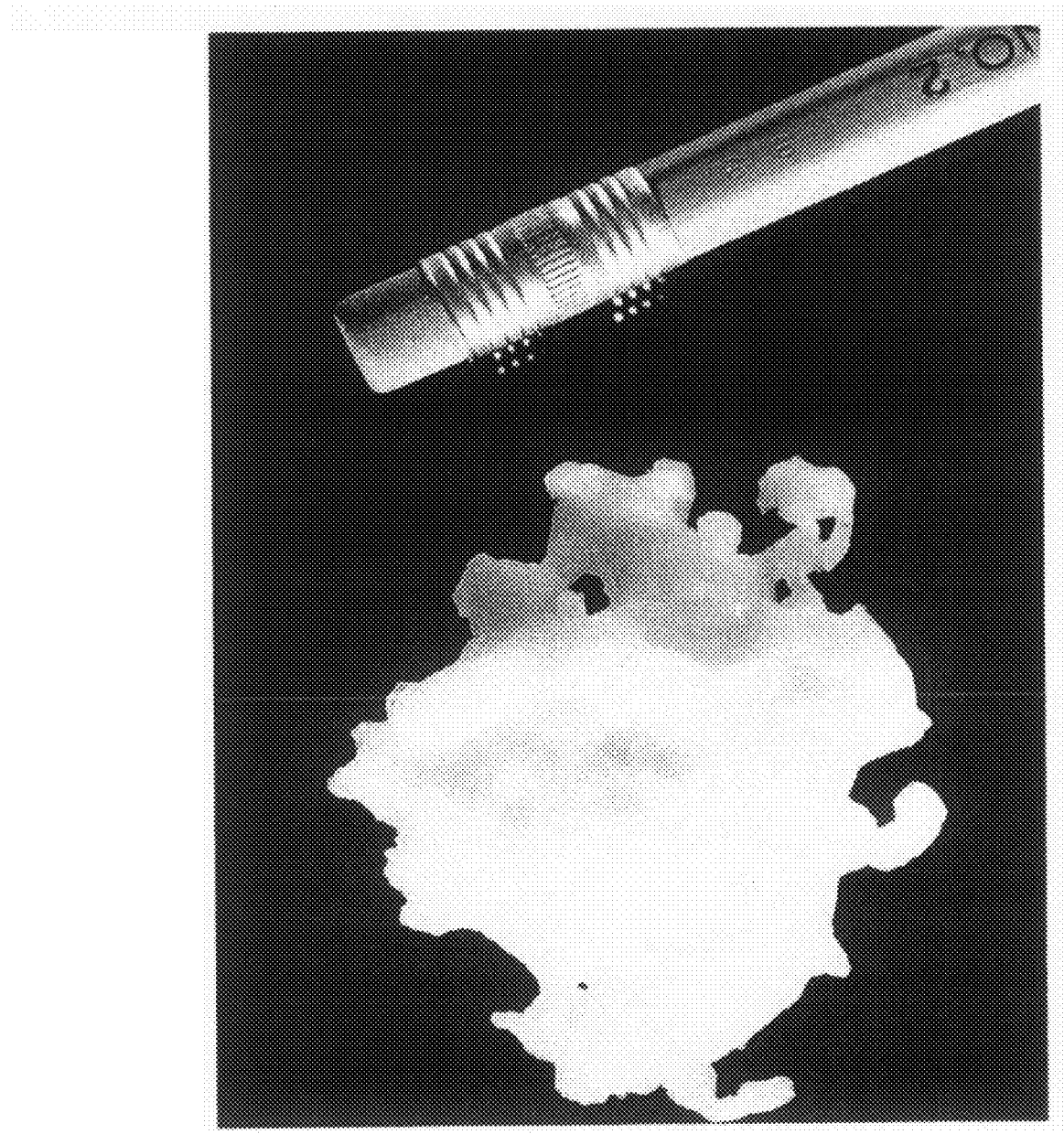
FIG. 4 is a photograph of the sterolithography model. The actual model was built to a scale of 300:1 and has a volume of 3.44 $cm^3$.

FIG. 4 shows the actual model described above built to a scale of 300:1 and has a volume of 3.44 cm$^3$. The running time for this sample was 2.3 hours, using a FDM 2000 stereolithography machine (Stratasys, Ontario CA). The orientation of this photography is similar but not identical to the orientation shown in FIGS. 2 and 3.

EXAMPLE 4

Experimental Design of the Retractometer
Principle of Operation

The performance of the device of this invention is based on the Laplace principle, in which the tension developed by the contraction of a sheet of platelets during clot retraction is transformed into an increase in pressure inside a semispherical flexible membrane.

Figure 5:
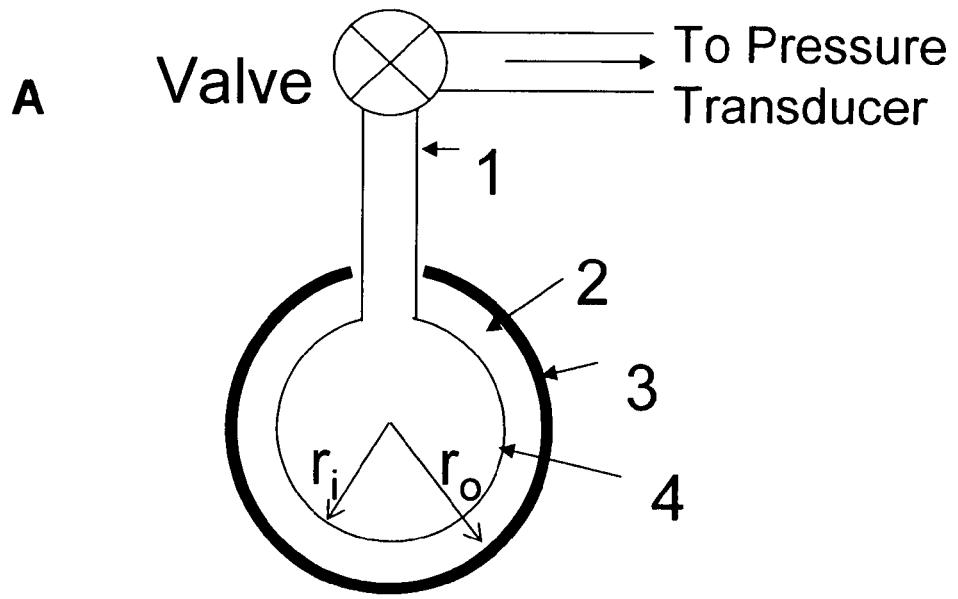
FIG. 5 is a diagrammatic representation of two alternative designs for the retractometer of this invention. Top panel (A) is a design in which the individual retractometers are connected through a system of communicating vessels sharing a common pressure transducer. This design allows the simultaneous measurement of several samples. Bottom panel (B), is an alternate design having a clay plug closing the air filled capillary tube, which the operator "snaps" by bending it around the etching before starting the reading. The fluid inside the capillary then reaches the "zero level" corresponding to the hydrostatic pressure of the system. This design allows the direct measurement of the pressure without the need of electronics.
Figure 5:
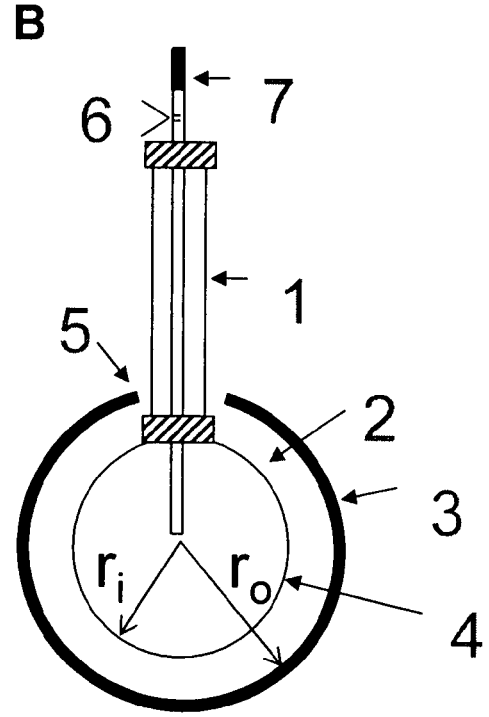

The geometry of the proposed device is the following. Let $r_o$ be the radius of a spherical container and $r_i$ the radius of a concentrical spherical membrane as shown in FIGS. 5 (A and B), $r_o > r_i$, $h = r_o - r_i$; $r_o$, $r_i \gg h$.

Two Alternative Designs for the Retractometer.

Two alternate embodiments of the retractometer of this invention are shown in FIG. 5AB. Top panel (A), is a design in which the individual retractometers can be connected through a system of communicating vessels sharing a common pressure transducer. This design allows the simultaneous measurement of several samples. In Figure A, prior to clotting, a blood sample is placed inside (2) the rigid reservoir (3). The thickness of the sample at 2 is $h = r_o - r_i$. A thin layer of mineral oil (light white oil, Sigma) is placed on top of the blood sample to avoid evaporation. As tension along the wall of the flexible membrane (4) increases due to clot retraction, the pressure inside the tube (1) increases.

Bottom panel (B) is a design in which the operator "snaps" the clay plug (7) of the air filled capillary tube, by bending it around the etching (scoring) (6) before starting the reading. Then the fluid inside the capillary reaches the "zero level" corresponding to the hydrostatic pressure of the system (details of the filling of the flexible membrane are given hereinbelow). The filling fluid of the flexible membrane may contain a coloring agent for easier visualization. The presence of the plug (7) prevents both fluid evaporation and changes in the fluid level by manipulation of the retractometer. This design allows the direct measurement of the pressure without the need of electronics.

Figure 6:
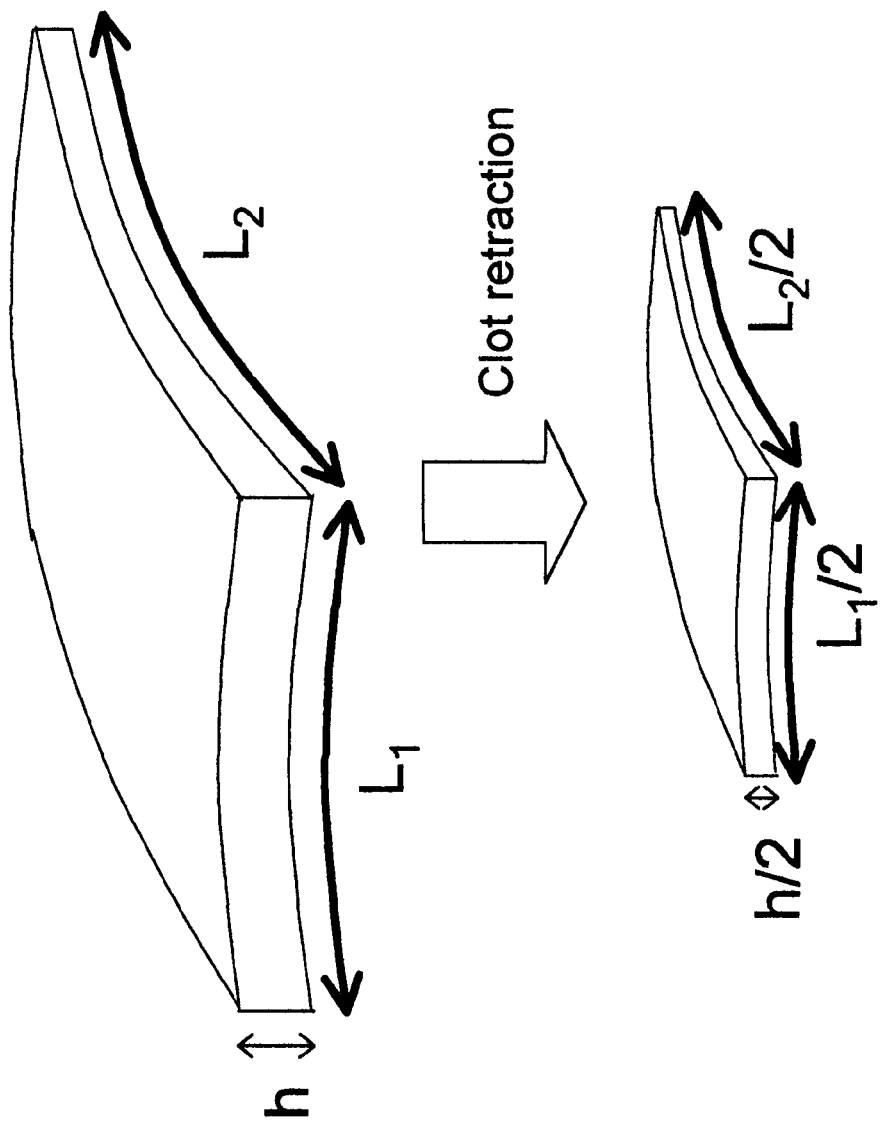
FIG. 6 is a diagram showing the contracting element. The upper panel of the figure represents the fibrin network before platelet contraction.

FIG. 6 is a diagrammatic representation of the contracting element described in the body of the text. The upper object of FIG. 6 represents the fibrin network before platelet contraction. As an example, FIG. 6 shows an isotropic retraction with a longitudinal strain of −0.5. The strain g is defined as $g=(L-L_0)/L_0$, where L is the length at the end of the deformation, and $L_0$ is the initial length. The bottom object shows the result of the isotropic contraction.

An important consideration in the design and performance of the retractometer device is that when the shell element described in FIG. 6 contracts, the only changes that contribute to an increase in the tension in the contracting element are L1 and L2. A contraction in h does not contribute to development of tension on the system described in FIG. 5. This concept is detailed in FIG. 7.

Figure 7:
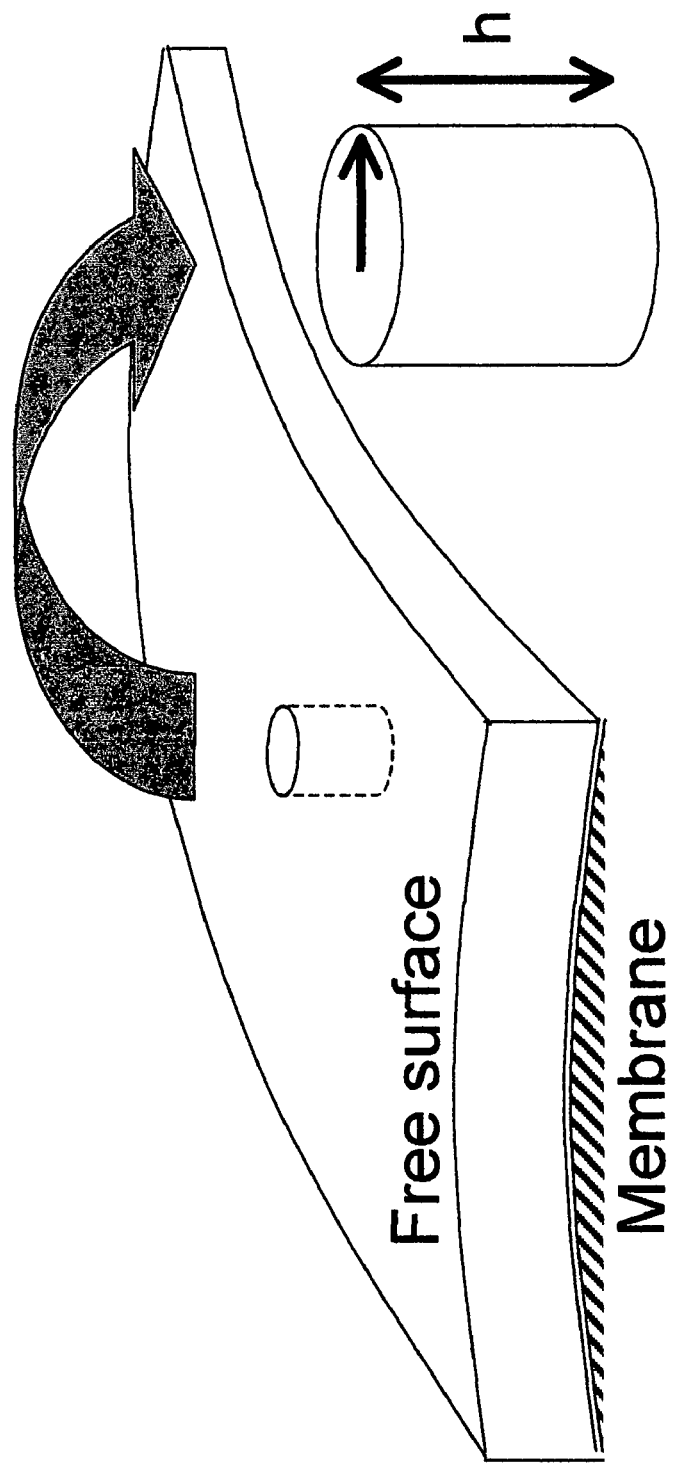
FIG. 7 diagrammatically represents the origin of the forces developed by platelet contraction within a retractometer of this invention. When the fibrin network contracts, tension develops along the surface of the element, due to the "pull" between the contracting elements.

FIG. 7 is a diagram representing the origin of the forces developed by platelet contraction in a retractometer. When the fibrin network contracts, tension develops along the surface of the element, due to the "pull" between the contracting elements. Because the outer surface of the contracting element is free, the contraction of the element along the thickness h results in a decrease in volume and not a modification of tension on the contracting element. In order to better represent this concept, the diagram on the right shows a free body taken from the contracting element. A change in radius of the cylindrical component shown results in an increase in tension along the surface as shown, while a change in height (h) does not modify the tension along the surface of the plate.

Figure 8:
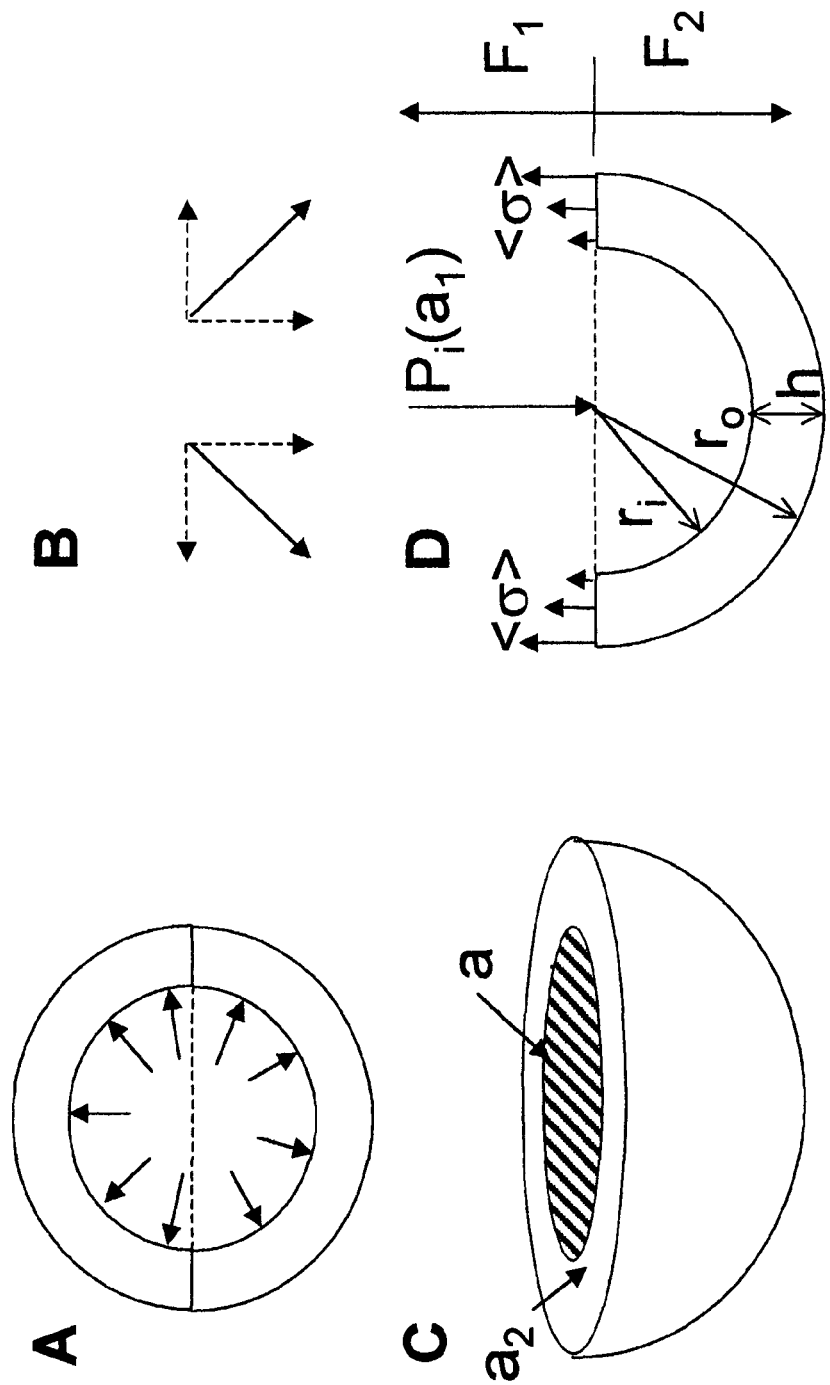
FIG. 8 is a force analysis of the retractometer. A is a diametrical cross-section in a plane passing through the center of the sphere. B is a geometrical representation of two arbitrary but symmetrical vectors acting on the unit represented in A.
Figure 9:
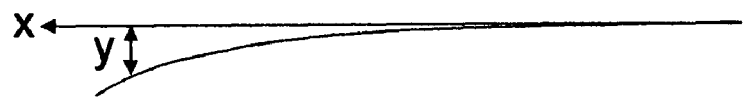
FIG. 9 shows the mechanical model comprising a cantilever beam clamped at one end, subject to a constant bending moment.

In order to calculate the magnitude by which a variation in the tension of the clot will result in a variation of internal pressure in the device shown in FIG. 5, it is helpful to use a free body diagram as shown in FIG. 8.

FIG. 8 represents a force analysis of the retractometer of this invention. The flexible membrane of the retractometer is modeled for this analysis as a perfect sphere. A is a diametrical cross-section in a plane passing through the center of the sphere as shown. The resultant inner pressure Pi is homogeneously distributed on the inner surface of the retractometer. The origin of all the vectors is the center of the sphere and all of them have the same magnitude. The dotted line in this panel shows the arbitrary cross-section where the analysis is performed.

B is a geometrical representation of two arbitrary but symmetrical vectors acting on the unit represented in A. Notice that the horizontal components (parallel to the cross-section shown in A with the dotted line) of these vectors cancel each other, the vertical component (normal to our arbitrary section shown in A) does not cancel by any of the vectors acting on the lower half of the sphere. Therefore, for the force analysis, the only vectoral components of the force resultant of Pi acting on the surface are normal to the cross section shown in A. These vectors act on the area $a_1$ shown in C, and $a_2$ is the sectional area of the wall of the sphere. D is a free body diagram of a thin slice of the body shown in C cut by two parallel planes at a small distance apart, one on each side of the center of the sphere. The circumferential stress F is a stress acting on, and normal to, the cross-sectional plane. <F> is the average value of F, which is non-uniform across the thickness of the wall. The value of <F> is computed hereinbelow. The vectors on the right side of D show the condition of equilibrium. As explained above, the force acting vertically and downwards ($F_2$) is computed as the pressure acting on $a_1$, or $Pi(a_1)$ and $F_2 = Pi(a1) = Pi\pi r_i^2$. The area of the wall of the contractile element is $Br_o^2 - Br_i^2$ The resultant tensile force due to clot retraction in this particular geometry is $F_1 = B(r_o^2 - r_i^2)$<F>. The balance of the forces in equilibrium requires, therefore, that F1=F2, or:

$$\pi(r_o^2 - r_i^2)\langle\sigma\rangle = \pi r_i^2 P_i \qquad (D:1)$$

or:

$$\langle\sigma\rangle = P_i \frac{r_i^2}{r_o^2 - r_i^2} = \frac{r_i^2 P_i}{h(r_o + r_i)} \qquad (D:2)$$

Therefore, the average tensile force can be easily calculated based on the measurement of the hydrostatic pressure inside the compartment defined by the flexible membrane.

This analysis is exact for a perfect sphere. Although the retractometer deviates from this uniform stress field in the area where the flexible membrane attaches to the capillary tube or connecting tube, the stress analysis is an excellent approximation at the operational level and it is valid for the purposes of the design presented in this description.

In order to be able to calibrate their retractometer and compare it with other known experimental models, Inventors decided to implement a system described by others (17), in which a cylindrical clot is immersed in ice-cold buffer to prevent platelet contraction. The clots are then anchored and held vertically to the bottom of the container at their lower end and to a force transducer to the upper end of the clot.

Force Transducer:

An isotonic force transducer was implemented. The system is based on the single supported beam principle. The mechanical model is a cantilever beam clamped at one end, subject to a constant bending moment. According to the following description:

The equation that dictates the behavior of the beam is:

$$\frac{d^2 y}{dx^2} = \frac{1}{EI} M(x) \qquad (D:3)$$

where: M is the bending moment imposed by the load on the cantilevered beam, E is Young's modulus, I is a property of the cross-sectional geometry of the beam, the term on the left is the deflection of the beam (assuming a deflection much smaller than the length of the beam).

The deflection y(x) can be calculated by using:

$$EI\frac{d^2 y}{dx^2} = M, \; EI\frac{d^3 y}{dx^3} = S \qquad (D:4,5)$$

where S is the transverse shear. The bending moment and the transverse shear are related to the lateral load by:

$$\frac{dM}{dx} =, \; \frac{dS}{dx} = w \qquad (D:6,7)$$

$$\frac{d^2 y}{dx^2} = \frac{1}{EI} M(x)$$

Where w is the lateral load per unit length.

Because a small curvature is assumed, and the slope of the deflection is finite, the equation to be used instead of D:3 is:

$$\frac{d^2 y}{dx^2}\left[1 + \left(\frac{dy}{dx}\right)^2\right]^{-\frac{3}{2}} = \frac{M(x)}{EI} \qquad (D:8)$$

Integration of equation D:8 yields:

$$y(x) = \frac{M}{EI}\frac{x^2}{2} + Ax + B \qquad (D:9)$$

Therefore, for a load imposed at a fixed distance in x, for a constant bending moment, and for a small deflection, the deflection is a linear function of the moment.

For the implementation of the force transducer, Inventors used a borosilicate glass rod, with a length of 15 cm and a diameter of 1 mm. Due to the relative length of the rod, deflections up to a maximum of 2 cm can be considered small.

Figure 10:
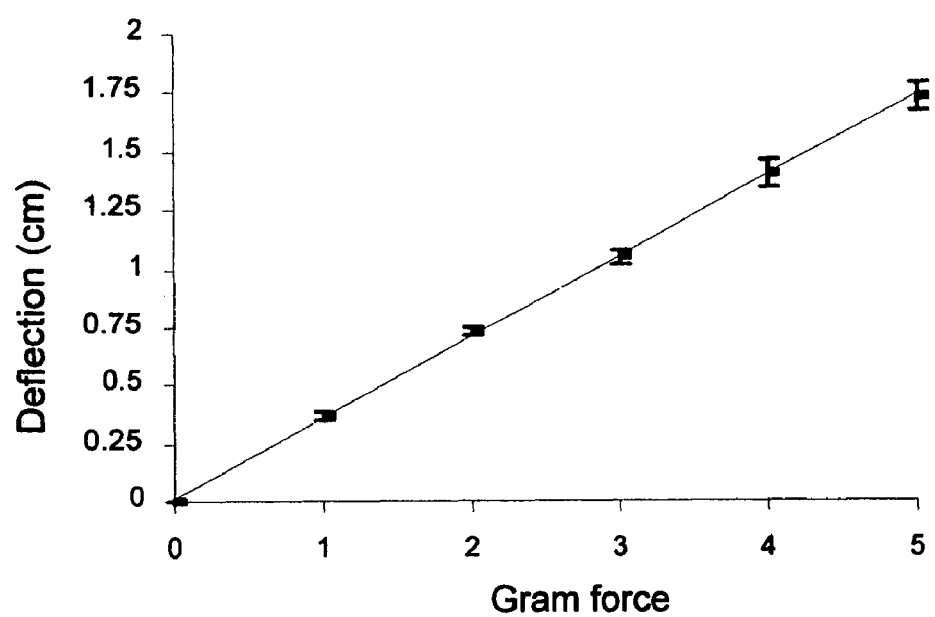
FIG. 10 shows the calibration graph of a single cantilevered transducer. Steps of 1 gram were used in the calibration. The means of the experimental points are shown with their corresponding standard error of the mean. The continuous line corresponds to the linear regression of the measured points. The correlation coefficient calculated is $r^2=0.9995$. The force resolution of the transducer is $2.85 \times 10^{-4}$ gram force.

The results of the calibration experiments are shown in FIG. 10. The range tested was from 0 to 5 gram force. This range proved to be adequate for the experimental conditions. FIG. 10 shows the calibration graph of a single cantilevered transducer that is part of this invention. Steps of 1 gram were used in the calibration. The means of the experimental points are shown with their corresponding standard error of the mean. The continuous line corresponds to the linear regression of the measured points. The correlation coefficient calculated is $r^2=0.9995$. The force resolution of this transducer is $2.85\times10^{-4}$ gram force.

Results

EXAMPLE 5

Fabrication of the Retractometer

Fabrication of the retractometer required research and development in the following areas:

1) Manufacturing of the flexible membranes. Which is subsequently divided in two steps:
   a) Fabrication of a suitable immersion mold
   b) Fabrication of the membranes
2) Filling of the membranes. This step is necessary to assure that the internal pressure of the membranes corresponds to the hydrostatic pressure of the fluid around them, during operation.
3) Adjusting of the fluid level inside the capillary at "zero pressure" level. This step is necessary for the operator to see the fluid level above the capillary holders.
4) Calibration of the system and comparison with an alternative method. The alternative method will be to measure directly the force developed by a cylindrical clot made with platelet rich plasma of the same donor to serve as our "gold standard."

Fabrication of a Suitable Immersion Mold

Figure 11:
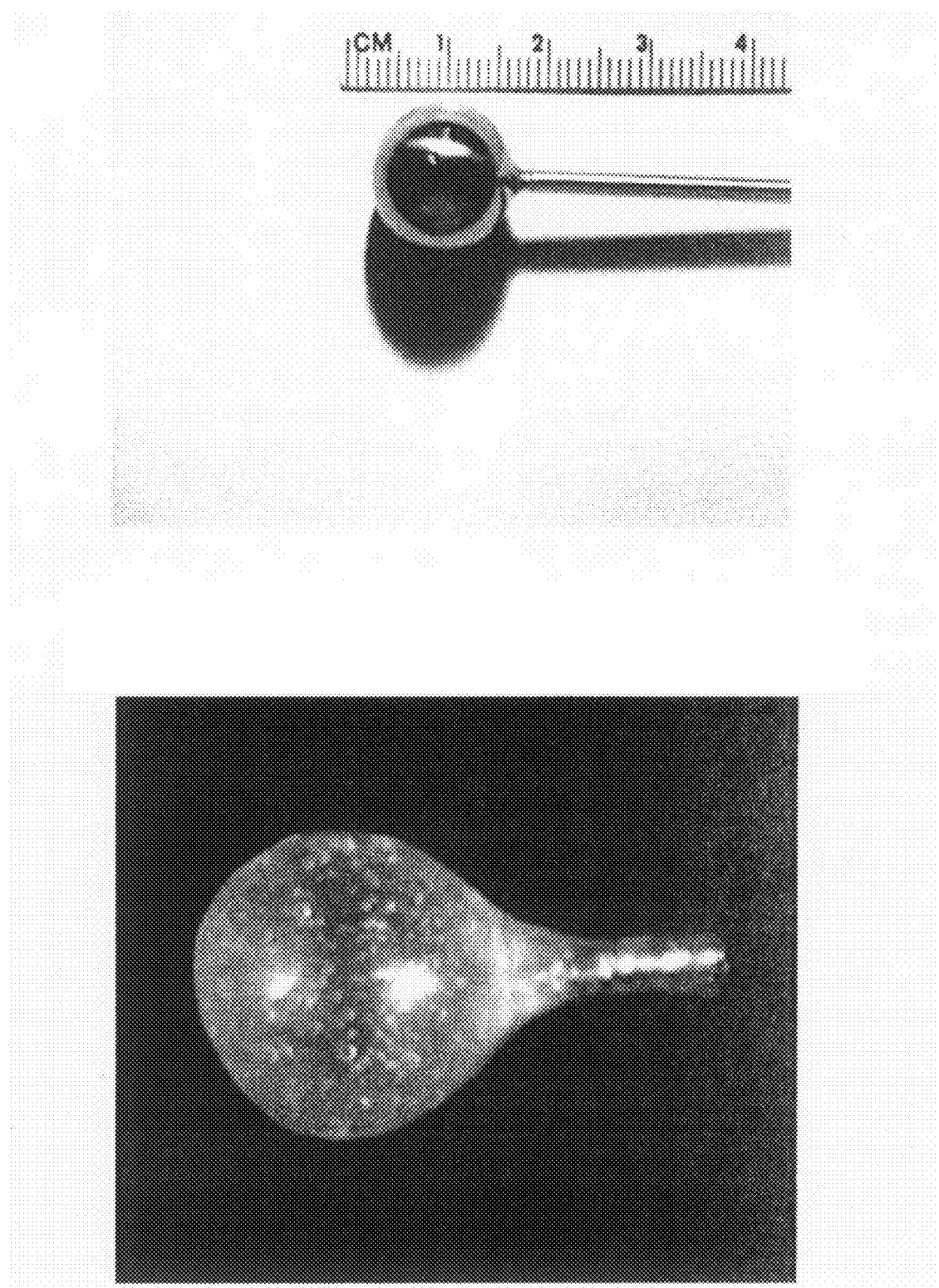
FIG. 11 Top: is a photograph of one embodiment of an immersion mold. The prototype shown here was manufactured from stainless steel. Bottom: is a prototype of the flexible membrane of this invention.

The first step in manufacturing of the flexible membrane is the fabrication of a suitable immersion mold. In a preliminary phase, Inventors fabricated a prototype mold from stainless steel. Turning now to FIG. 11, the top panel is a photograph of the stainless steel immersion mold. Although the embodiment shown here was manufactured from stainless steel, it could likewise be made from any other suitable material. The ball has a diameter of 9/16" and the rod has a diameter of 3/32", but these could be of any suitable dimension. The bottom panel shows an embodiment of the flexible membrane. This prototype was made to show the feasibility of fabrication using the immersion mold shown on top. This prototype embodiment was fabricated using urethane, but any other suitable material could be used. Due to the transparency of the material it is easy to study the thickness of the membrane. The figure shows an even thickness of the material along the spherical region of the membrane. However, this fabrication technique yields an increase in thickness around the region of the neck (white arrow). It can be concluded from the stress analysis shown in FIG. 8, that the stresses on the wall are uniformly distributed along the flexible membrane, except around the point of insertion of the capillary tube. Therefore, it is expected that this thicker region will not have an important impact in the performance of the retractometer.

Fabrication of the Membranes.

The membranes would preferably be fabricated by experts in dip molding technology, for example by ACC Automation (Akron, Ohio). For this application, their 4-axis dipping system would be particularly suitable. Briefly, the system has 4 axis of operation (vertical, horizontal/pallet rotate and form spin), allowing the membrane coating to be uniform along the surface of the mold. The equipment has a vertical stroke of 30 inches, a vertical axis speed range of 0.01-12 inch/sec, with 0.001 inch/sec speed increments. Rotate axis positional range is 1440 degrees in 1 degree positional increments. Rotate axis speed range is 0.1-60 degrees/sec in 0.1 degree speed increments. Spin speed range is 10-100 RPM in 1 RPM increments. Horizontal axis position is 18 inches in 0.01 inch positional increments. Horizontal axis speed range is 0.01-4.0 inches/sec in 0.001 inches/sec/Maximum payload capacity of 10 pounds.

The membranes are dried in an integrated force air convection electric oven, with programmable temperature control up to 200° C. The forms are spun in the oven to increase drying uniformity.

The membranes are fabricated using two coats of latex without thickening agent, in a similar fashion to fabricating condoms. Uniformity in thickness and mechanical properties of the membranes are highly reproducible.

The second step is to develop a suitable method for the filling of the membranes.

Preparation of the Membrane Prior to the Final Assembly of the Retractometer.

Figure 12:
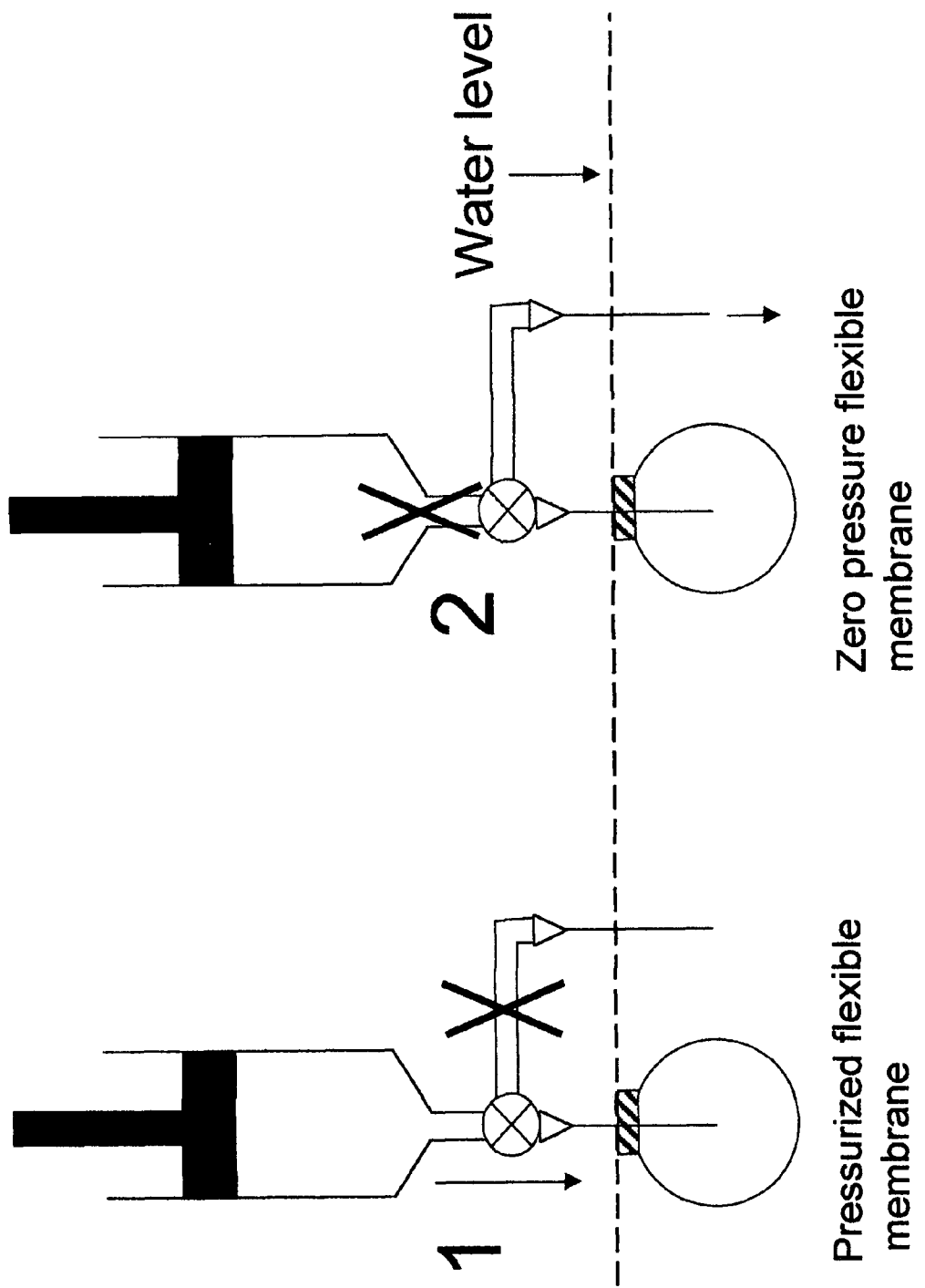
FIG. 12 is a graphic representation of a method used to pressure condition the membrane.

In order to assure that the inner pressure of the membrane is in equilibrium with the surrounding fluid, Inventors implemented a simple technique shown in FIG. 12. In order to avoid slippage of the clots over the membrane surface during contraction, the membranes are coated with a suitable adhesive, for example, with a bovine collagen type I suspension as described elsewhere (2.5 mg/ml in 0.1 M acetic acid) (20). This method gave a firm adhesion of the clot onto latex membranes. It is expected that membranes of different materials may require other adhesives.

Membranes are pressure-conditioned as shown in FIG. 12. The flexible membrane is mounted on a sealing rubber stop with a needle inserted through it. The needle is connected to a two-way stop-cock, which in turn is connected to a syringe and another needle. The reach of both needles is the same. In a first step, the syringe is used to slightly pressurize the flexible membrane. In a second step, access to the syringe is closed and the two needles are allowed to equilibrate the inner membrane pressure and the ambient pressure by siphoning the fluids. This method is reliable in giving zero pressure readings with the use of a pressure transducer (Validyne DP15-22, controlled by a Validyne CD379) immediately after inflation.

The third step is the adjusting of the fluid level inside the capillary at "zero pressure" level. As seen in FIG. 5B, it would be desirable to control the level of the column inside the capillary to make the reading easier. The height of the column in a capillary tube is dictated by the expression:

$$h = \frac{2\gamma}{\rho g r} \cos\theta \qquad (D:10)$$

where, h is the height of the column, $\gamma$ is the surface tension of the fluid, $\rho$ is the density of the fluid, r is the radius of the capillary tube, and $\theta$ is the wetting angle. The pressure inside the flexible membrane of the retractometer, can be easily calculated with the expression $\Delta p = \rho g h$.

In order to make the retractometer more user-friendly, it is necessary to have a good "zero pressure" level inside the capillary, otherwise the reading error may increase. An easy way to do this is by proper choice of the capillary radius. The possibility of changing the angle of the meniscus $\theta$ in equation D:10, with the following method (21).

Hydrophilic Modification of the Capillaries

The glass capillaries are immersed in a 1% (w/w) NaOH water solution. The container is heated to near boiling (bubble formation starting) (approx 90° C.) and incubated for 10 minutes. The solution is removed, and the capillaries are allowed to cool to room temperature. The capillaries are then immersed in a 30% (w/w) $H_2O_2$ solution, and heated to near boiling (approx 90° C.) for one hour, washed five times with deionized, demineralized water, tap dried and placed in a drying oven (250° C.) for 12 hours. Column heights were improved from 16 mm (with a 0.75 radius, untreated capillary) to 60 mm (with a 0.5 mm radius, hydrophilic modified capillary).

The fourth step is the calibration of the retractometer and comparison of the results to an alternative, known method.

Figure 13:
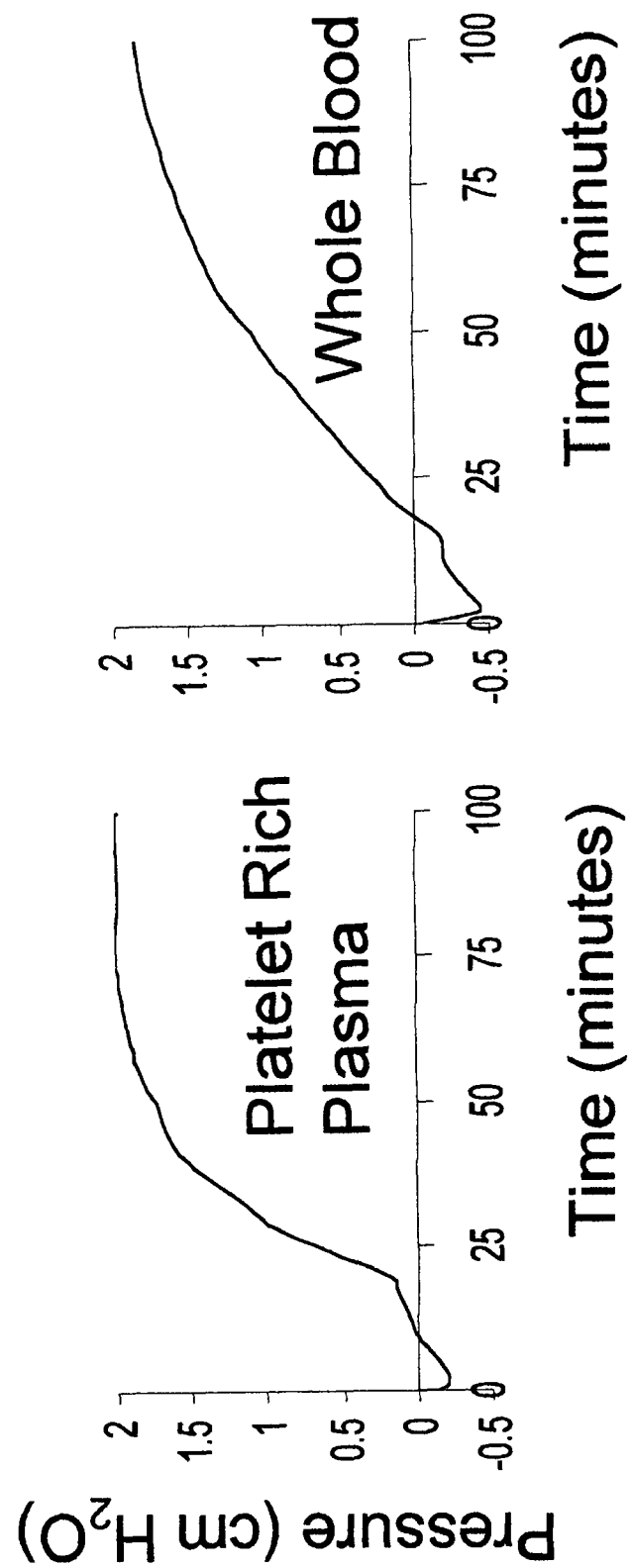
FIG. 13 depicts the results of a preliminary experiment to show the feasibility of the proposed methodology. For the experiment shown here the flexible membrane used was fabricated with latex with a thickness of 150 μm. Citrated blood (11 μM Sodium Citrate) was used.

In order to explore the feasibility of the methodology in the present invention, a prototype retractometer was implemented, as detailed in FIG. 5. For the setup of these preliminary experiments, it was decided to use a latex flexible membrane with a thickness of 150 µm. The pressure in both experiments was continuously recorded using a pressure transducer (Validyne DP15-22, controlled by a Validyne CD379). A citrated blood sample was separated into two aliquots, one aliquot was used to prepare a platelet-rich plasma sample by centrifugation at 150×g for 10 minutes. The other aliquot was used directly without enrichment. Prior to beginning the experiment, a sample (platelet rich plasma or blood) was supplemented with calcium to initiate coagulation. A solution of 0.2 M $CaCl_2$ at 42 µl/ml of blood and 65 µl/ml of platelet-rich plasma, the difference in volumes accounts for the inert volume occupied by red blood cells in the whole blood sample. During the experiment, samples were kept at 37° C. The results of these experiments are shown in FIG. 13. As predicted, platelet contractility results in an increase in the hydrostatic pressure inside the flexible membrane.

Figure 14:
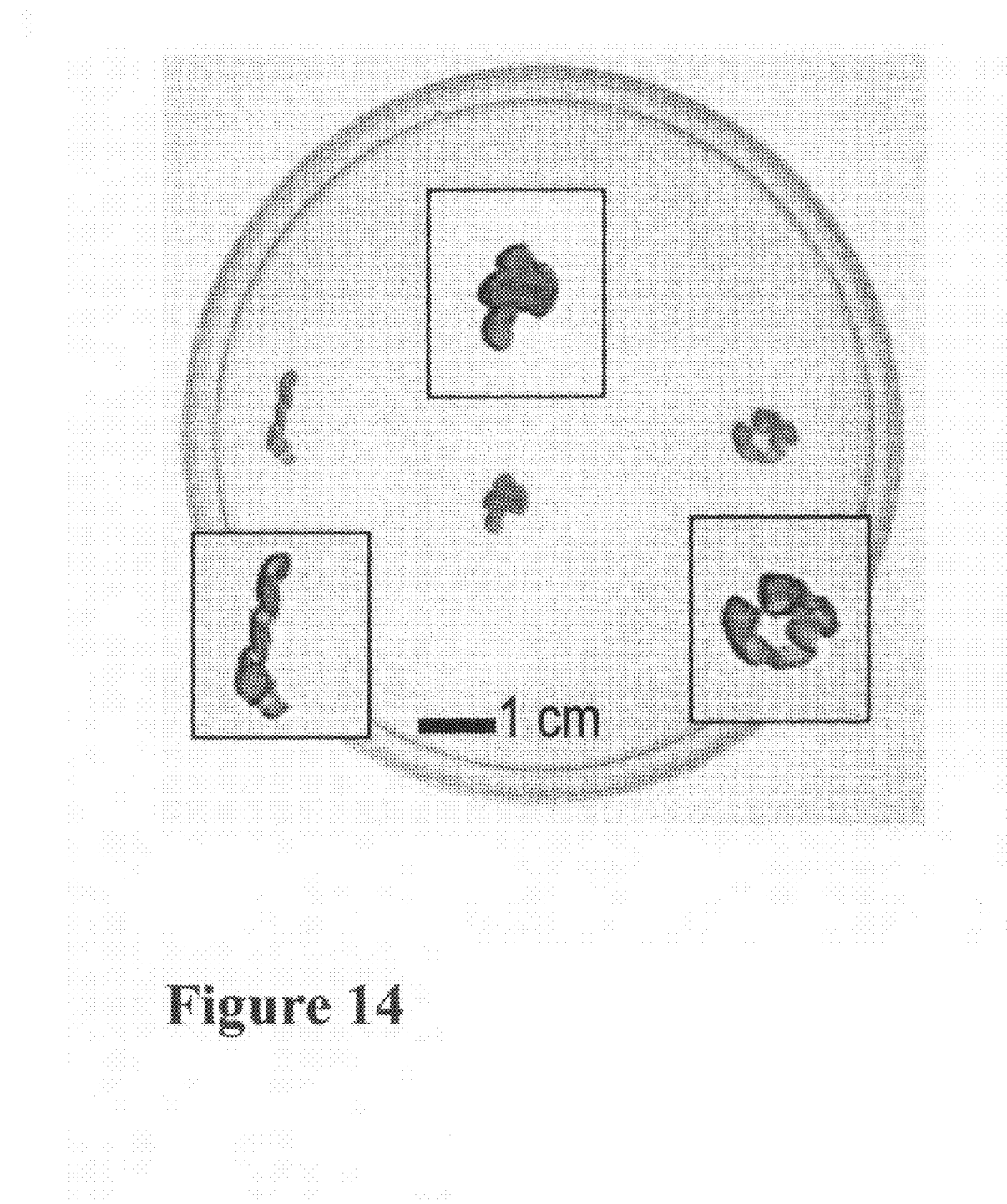
FIG. 14 illustrates the change in shape of the clots when separated from the membrane and cut open. The photograph shows a petri dish with three sections of the clot. A digitally enhanced magnification of the three samples shown is presented for better appreciation of the process.

In order to demonstrate that the increase in hydrostatic pressure shown in FIG. 13 was indeed due to an increase in the tension on the fibrin network, the retractometer was disassembled at the end of the experiment, the membrane and the clot were immersed in a phosphate buffered saline solution to avoid drying of the sample. The membrane and the attached fibrin clot were then sectioned in rings parallel to the equator, the rings were attached to ribbons and the clots were carefully separated from the latex membrane. The rationale for the cuts was to unveil the residual stresses in the clots. Cutting introduces new surfaces on which the traction is zero. Cutting an unloaded body without residual stress will not cause strain. If strain changes by cutting, there is residual stress. The results shown in FIG. 13 demonstrate the feasibility and validity of the principle of operation of the methodology. The stresses along the thickness of the clot are not uniform, due to the geometry of the retractometer. This lack of uniformity in stresses must, therefore, result in "shearing strain" across the thickness of the clot. This is seen macroscopically in FIG. 14 as twisting of the clots. FIG. 14 shows a petri dish with three sections of the clot. A digitally enhanced magnification of the three samples shown is presented for better appreciation of the process. It should be noted that the larger the deformation the larger is the residual stress. The large twisting deformation is due to the non-uniform increase in tension along the thickness of the wall of the clots.

An Alternative Method and Comparison of Results

Inventors decided to implement a method described by others (17) for calibration and comparison. The method is briefly described below.

Cylindrical clots are obtained by pouring a human platelet-rich plasma (PRP) suspension, immediately after thrombin addition, into cylindrical plastic molds (6 mm diameter and 5 cm in length). The molds are plugged at both ends with plastic plugs. The sides of the molds are slit for easier clot extraction, but the ends meet in a manner such that drying out is prevented. After 10 minutes, the clot cylinders are poured into a Petri dish containing ice cold Tyrode solution to inhibit contraction. The clots are then tied at one end with a cotton thread to a rigid stainless steel support and the other end to a force transducer as described hereinabove.

In order to compare the experimental results of clot retraction with the two different setups, it is helpful to link the two methods by the stress generated by platelet contraction.

Figure 15:
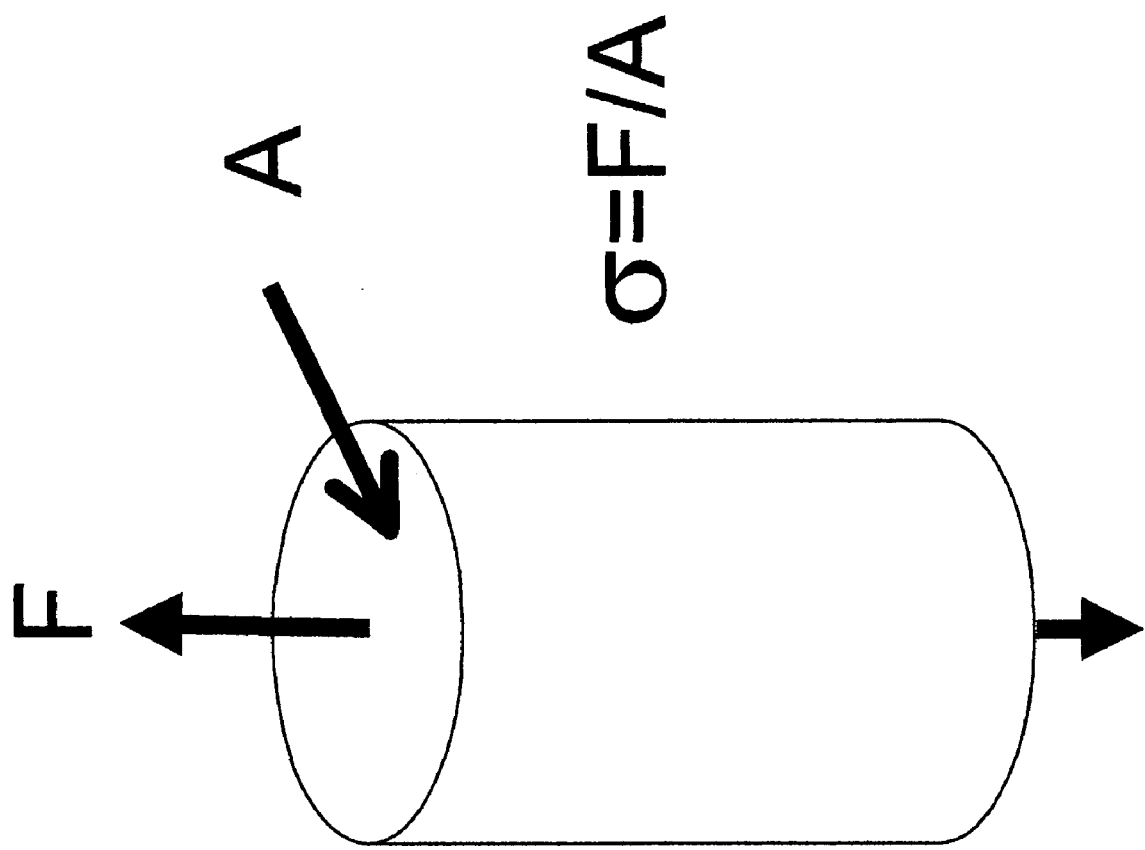
FIG. 15 is a schematic of the geometry of the cylindrical clot during contraction. The contraction of the clot is considered to be isotropic (17). The force F is measured directly by the force transducer. The area A can be directly calculated from the measurement of the clot diameter. The stress (F) can be estimated from this simple model.

FIG. 15 outlines schematically the geometry of the cylindrical clot during contraction. The contraction of the clot is considered to be isotropic (17). The force F is directly measured by the force transducer. The area A can be directly calculated from the measurement of the clot diameter. The stress (F) can be estimated from this simple model.

Assuming that the stress generated by the platelets is the same in the two retractometers, it follows from equation D:2 and FIG. 15 that:

$$\frac{F}{A} = P_i \frac{r_i^2}{r_0^2 - r_i^2} \quad (D:11)$$

Regarding the units of both expressions: $P_i$ is given in cm $H_2O$: 1 cm $H_2O$=1 gf/$cm^2$.

Figure 16:
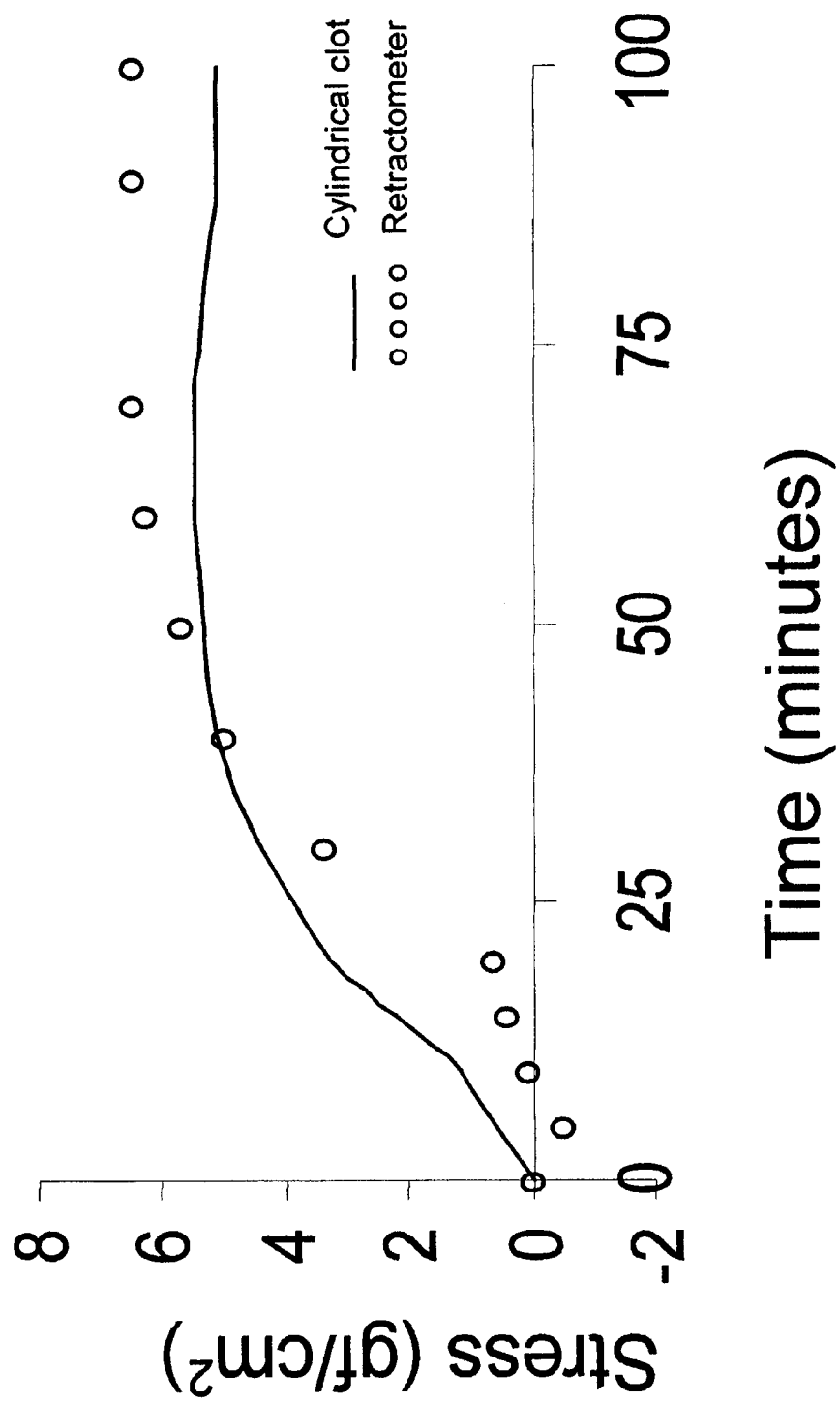
FIG. 16 is a comparison of the two methods used in this description. Both experiments were performed using platelet rich plasma.

Turning now to FIG. 16 for a comparison between the two methods used. Both experiments were performed using platelet rich plasma. In order to compare the results, data are presented in terms of the stress as suggested by equation D:11. The solid line shows the results obtained with the cylindrical clot and the circles represent the experimental data points obtained with the method of this invention.

The values calculated by equation D:11 are highly dependent on the accurate measurement of the radii in both, the cylindrical clot system and the retractometer of this invention.

Immediately after the mechanical test, the clots are fixed in 1.25% (vol/vol) glutaraldehyde diluted in 0.1M phosphate buffer (pH 7.2) for one hour at room temperature. The clots are then postfixed in 1% (wt/vol) osmic acid containing 1.5% potassium ferrocyanide for one hour at 4° C. Subsequently, they are dehydrated using graded alcohols and propylene oxide before being embedded in Epon. We have successfully used this technique to estimate the ultrastructure of fibrin clot deformation (22). This step is done only for calibration purposes and it is not intended to be used as a routine in the future.

EXAMPLE 6

Described below is an electronic circuit designed to operate the individual solenoid valves controlling the hydraulics of the communicating vessels for the embodiment shown in FIG. 5 A.

Figure 17:
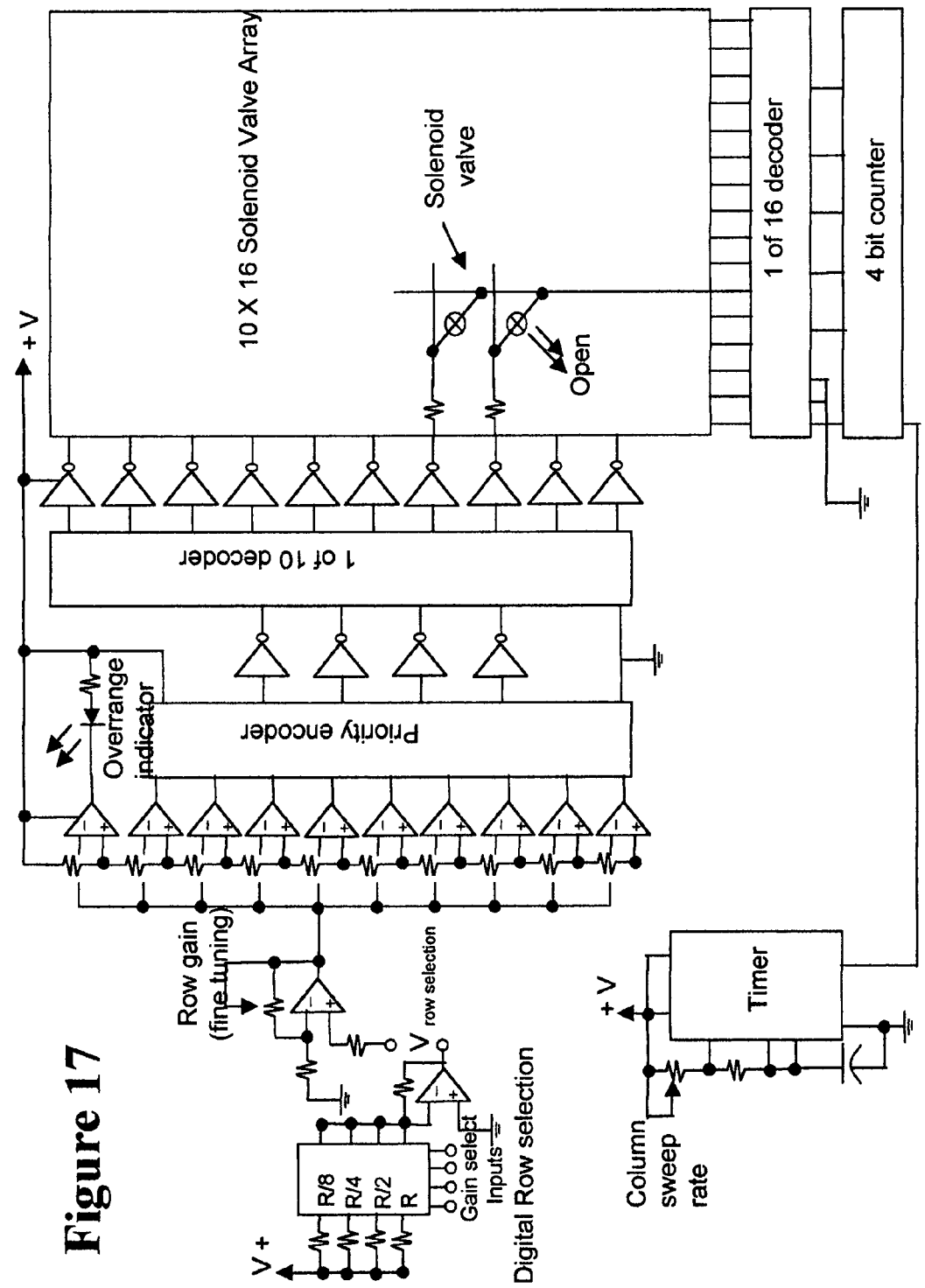
FIG. 17 is a schematic diagram of an electronic solenoid valve controller useful in simultaneous processing of many samples.

The electronic solenoid valve controller circuit is shown in FIG. 17. For the circuit shown here, a 10×16 array was implemented. The circuit labeled digital row selection is meant for an alternative computer control. When a word is written to the gain select input of the CMOS circuit shown (analog to CD4066), a voltage is generated at the output of the circuit, which is used to select the row on the right hand circuits. In principle, the voltage used for row selection can also be selected manually via a potentiometer part of a voltage divider. Implementation of these circuits allows the operator to select the row either manually or via digital input. The operational amplifier (Row Gain) is intended to give the maximal gain of the voltage divider for row selection. The use of this is to select manually the maximal row number to be read in a given cycle. This non-inverting input of the operation amplifier (op amp) is amplified and sent to an A/D converter, implemented by the comparators and the priority encoder. Should the control be exclusively digital, this part of the circuit is obsolete, in which case the already digital input should be sent directly to the 1 of 10 decoder (10 is arbitrarily chosen in this case, and the total number of rows can be different). The final result of this architecture is that only one row is activated at a time.

For column selection, Inventors chose to add a timer assuming that the column selection is done in a continuous sweep. The timer shown in the lower left corner of the diagram (FIG. 17) has a feedback loop controlled by a potentiometer that allows the operator to control the sweeping rate. The output of the timer serves as the input for a 4-bit counter, the output of the counter is input into a 1 of 16 decoder to select only one column at a time.

EXAMPLE 7

Figure 18:
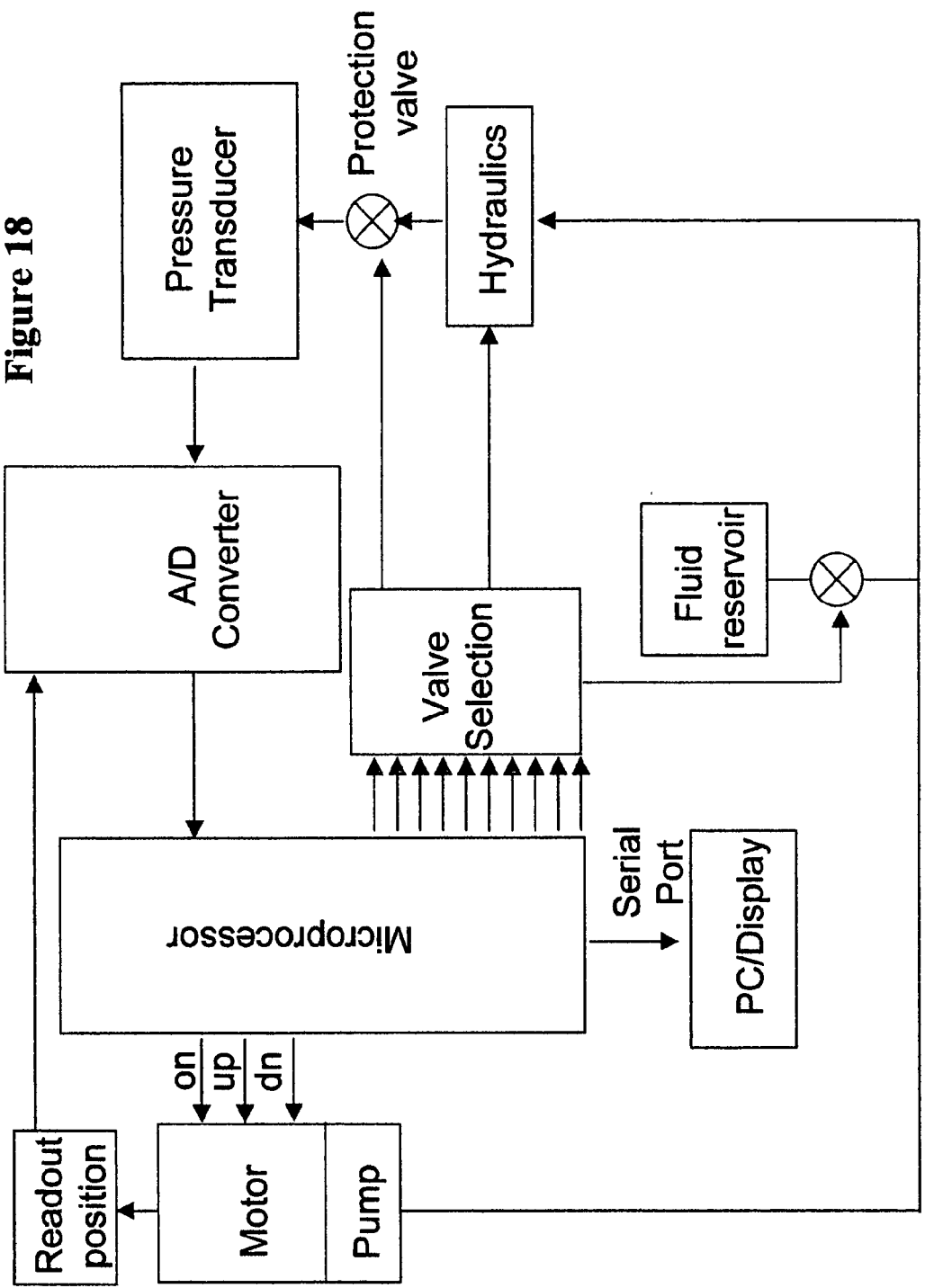
FIG. 18 is a schematic representation of the fully automated system apparatus that can greatly increase the speed and ease of measuring platelet contractility in a number of retractometers, each having the same or different sample. Such a system is highly useful in screening populations and effectiveness of various drugs.

Another embodiment of an electronic solenoid valve controller of this invention is shown in FIG. 18. For the example shown here, an 8051 microprocessor is used. Three pins of the microprocessor actuate a syringe pump. Pin one is used to turn the pump on and the other two to move the pump piston either up or down. The pump is directly connected to the hydraulics (retractometers) of the system. The motor of the pump is connected to a voltage divider that yields a voltage used to establish the position of the piston of the pump. This readout position voltage is entered through an analog to digital (A/D) converter to the microprocessor. Other pins of the microprocessor are connected to each one of the solenoid valves used in the array.

In this example, a series of eight valves are used to measure each one of the retractometer samples and two others are used to provide protection to the system. One of the protection valves is located at the entrance of the pressure transducer, and its role is to prevent damage to the system due to the operation of the pump. The other valve is located to provide access to a fluid reservoir. This valve is used in this example to fill the syringe prior to the beginning of the experiments. The output voltage of the pressure transducer is entered into the A/D converter and subsequently to the microprocessor. For this example, the subroutines were burnt into the microprocessor. In an initial stage of operation, the microprocessor reads all initial pressures of all the samples by opening each individual sample valve, followed by opening of the protection valve. The voltage from the pressure transducer is measured and stored in the temporary memory of the microprocessor. This process is repeated until all the initial pressure values are registered.

In the following cycles, the previous pressure value for the valve that will be measured is taken as the target value. Then the value of the hydraulics is taken, having only the protection valve opened. The pump is then actuated (either up or down depending on the relative value of the target pressure) until the target pressure value is reached. The sample valve is then opened, the pressure is measured, and the sample valve is closed. The measured values are sent to a text file in a PC computer via a serial port. The new measured value for each valve becomes the next target value. These cycles are repeated until the end of the experiment.

While the present invention has now been described in terms of certain preferred embodiments, and exemplified with respect thereto, one skilled in the art will readily appreciate that various modifications, changes, omissions and substitutions may be made without departing from the spirit thereof. It is intended, therefore, that the present invention be limited solely by the scope of the following claims.

REFERENCES

1. Carr, M. E. and Zekert, S. L. 1991. Measurement of Platelet-Mediated Force Development During Plasma Clot Formation. *Am. J. Med. Sci.* 302:13-18.
2. Bromberg, M. E., Sevy, R. W., Daniel, J. L., and Salganicoff, L. 1985. Role of myosin phosphorylation in contractility of a platelet aggregate. *Am. J. Physiol.* 249:C297-C303.
3. Savage, B., Saldivar, E., and Ruggeri, Z. M. 1996. Initiation of platelet adhesion by arrest onto fibrinogen or translocation on von Willebrand factor. *Cell* 84:289-297.
4. Carr, M. E. Jr. and Carr, S. L. 1995. Fibrin structure and concentration alter clot elastic modulus but do not alter platelet mediated force development. *Blood Coagul. Fibrinolysis* 6:79-86.
5. Hartwig, J. H., Bokoch, G. M., Carpenter, C. L., Janmey, P. A., Taylor, L. A., Toker, A., and Stossel, T. P. 1995. Thrombin receptor ligation and activated rac uncap actin filament barbed ends through phosphoinositide synthesis in permeabilized human platelets. *Cell* 82:643-653.
6. Stossel, T. P. 1993. On the crawling of animal cells. *Science* 260: 1086-1094.
7. Nachmias, V. T. 1993. Small actin-binding proteins: The □-thymosin family. *Curr. Opin. Cell Biol.* 5:56-62.
8. Hartwig, J. H. and DeSisto, M. 1991. The cytoskeleton of the resting human blood platelet: Structure of the membrane skeleton and its attachment of actin filaments. *J. Cell Biol.* 112:407-425.
9. Hartwig, J. H. 1992. Mechanisms of actin rearrangements mediating platelet activation. *J. Cell Biol.* 118:1421-1442.
10. Fox, J. E. B. 1993. The platelet cytoskeleton. *Thromb. Haemost.* 70:884-893.
11. Nachmias, V. T. and Golla, R. 1991. Vinculin in relation to stress fibers in spread platelets. *Cell Motil Cytoskeleton* 20:190-202.
12. Machesky, L. M. and Hall, A. 1996. Rho: a connection between membrane receptor signalling and the cytoskeleton. *Trends Cell Biol* 6:304-310.
13. Carr, M. E. Jr. and Zekert, S. L. 1994. Abnormal clot retraction, altered fibrin structure, and normal platelet function in multiple myeloma. *American Physiological Society* H1195-H1201.
14. Carr, M. E. and Zekert, S. L. 1991. Force monitoring of clot retraction during DDAVP therapy for the qualitative platelet disorder of uraemia: report of a case. *Blood Coagul. Fibrinolysis* 2:303-308.
15. Holme, S., Heaton, W. A., and Whitley, P. 1990. Platelet storage lesions in second-generation containers: correlation with in vivo behavior with storage up to 14 days. *Vox Sang.* 59:12-8.
16. Didisheim, P. and Bunting, D. 1966. Abnormal platelet function in myelofibrosis. *Am. J. Clin. Pathol.* 45:566-573.
17. Cohen, I. and De Vries, A. 1973. Platelet contractile regulation in an isometric system. *Nature* 246:36-37.
18. Jen, C. J. and McIntire, L. V. 1982. The structural properties and contractile force of a clot. *Cell Motil Cytoskeleton* 2:445-452.
19. Savage, B., Sixma J. J., and Ruggeri, M. 2002. Functional self-association of von Willebrand factor during platelet adhesion under flow. *Proceedings of the National Academy of Sciences* 99:425-430.
20. Ruggeri, Z. M., Dent, J. A., and Saldivar, E. 1999. Contribution of distinct adhesive interactions to platelet aggregation in flowing blood. *Blood* 94:172-178.
21. Burns, N. L., Van Alstine, J. M., and Harris, J. M. 1995. Poly(ethylene glycol) grafted to quartz: Analysis in terms of a site-dissociation model of electroosmotic fluid flow. *Langmuir* 11:2768-2776.
22. Saldivar, E., Orje, J. N., and Ruggeri, Z. M. 2002. Tensile Destruction Test as an Estimation of Partial Proteolysis in Fibrin Clots. *Am. J. Hematol.* 71:119-127, 2002.

What is claimed is:

1. A method for automatically measuring a plurality of samples to determine strength of platelet contractility, comprising:

a first step of calibrating an automated system apparatus for measuring platelet contractility in plurality of samples, wherein a microprocessor reads all initial pressures in all retractometers sequentially by opening each solenoid valve, opening the protection valve, measuring the voltage in the pressure transducer, storing the measured value in the temporary memory of the microprocessor, wherein this process is repeated until all the initial pressure values are registered as target values for each of the retractometers;

a second step, wherein the value of the hydraulics is taken by opening the protection valve only, activating the pump until the target value is reached; and a third step of opening the sample valve, measuring the pressure, closing the sample valve, sending the measured values to a text file in a computer, wherein, the new measured value for each retractometer becomes the next target value, wherein said third step is repeated until all samples are measured; and wherein, said automated system apparatus comprises an array of retractometer units, each of which is a separate apparatus for measuring blood platelet contractility, comprising: a spherical rigid chamber having an opening in its upper aspect; a smaller, spherical, flexible membrane chamber, coated on its outer surface with a suitable adhesive to prevent slippage of a clot forming on said surface, placed concentrically within the rigid chamber creating a void space between the walls of the rigid and flexible chambers and having an opening in its upper aspect smaller than and coaxial to the opening in the rigid chamber and a first, attached contiguous tubular passage leading out of the flexible membrane chamber concentrically and in perpendicular axis through the opening in the rigid chamber, creating a void space that is isolated from the void space of the flexible membrane inner chamber; a two-way valve attached to the distal end of the tubular passage; a second tubular passage connected to the valve at one end and in perpendicular axis to the first passage; and a common pressure transducer connected to the other end of the second passage of each separate retractometer, wherein any force exerted on the flexible membrane chamber of each retractometer to alter its diameter would be measured by the common pressure transducer.

2. The method according to claim 1, wherein the strength of platelet contractility is useful in determining platelet activity in said plurality of samples.

3. The method according to claim 1, wherein the platelet contractility is useful in diagnosis or prognosis of various diseases in patients.

4. The method according to claim 2, wherein the platelet activity is useful in rapidly determining viability of platelets in plurality of stored blood products.

* * * * *